(12) United States Patent
Chaudhari et al.

(10) Patent No.: US 8,284,070 B2
(45) Date of Patent: Oct. 9, 2012

(54) ASSESSMENT DEVICE

(75) Inventors: Ajit Chaudhari, Columbus, OH (US); Christopher McKenzie, Lancaster, OH (US)

(73) Assignee: The Ohio State University, Columbus, OH (US)

( * ) Notice: Subject to any disclaimer, the term of this patent is extended or adjusted under 35 U.S.C. 154(b) by 311 days.

(21) Appl. No.: 12/600,123

(22) PCT Filed: May 14, 2008

(86) PCT No.: PCT/US2008/006104
§ 371 (c)(1),
(2), (4) Date: Feb. 23, 2010

(87) PCT Pub. No.: WO2008/143841
PCT Pub. Date: Nov. 27, 2008

(65) Prior Publication Data
US 2010/0156653 A1 Jun. 24, 2010

Related U.S. Application Data

(60) Provisional application No. 60/917,919, filed on May 14, 2007.

(51) Int. Cl.
*G08B 21/00* (2006.01)
(52) U.S. Cl. ............... 340/686.1; 340/573.1; 340/573.7; 702/153; 702/94
(58) Field of Classification Search ............... 340/573.1, 340/573.7, 686.1, 524; 600/595; 73/865.4; 702/153, 92, 94
See application file for complete search history.

(56) References Cited

U.S. PATENT DOCUMENTS

| | | | |
|---|---|---|---|
| 4,665,338 A | 5/1987 | Inaba et al. | |
| 4,665,388 A | 5/1987 | Ivie et al. | |
| 5,089,808 A | 2/1992 | Amirdash | |
| 5,128,655 A | 7/1992 | Shore | |
| 5,158,089 A * | 10/1992 | Swezey et al. | 600/595 |
| 5,221,088 A | 6/1993 | McTeigue et al. | |
| 5,300,921 A | 4/1994 | Hoch et al. | |
| 5,338,276 A | 8/1994 | Jull et al. | |
| 5,398,697 A | 3/1995 | Spielman | |
| 5,402,107 A | 3/1995 | Rencavage | |
| 5,430,435 A | 7/1995 | Hoch et al. | |
| 5,754,121 A * | 5/1998 | Ward et al. | 340/870.09 |
| 5,865,760 A | 2/1999 | Lidman et al. | |
| 5,887,351 A | 3/1999 | Arms et al. | |
| 5,930,741 A * | 7/1999 | Kramer | 702/153 |
| 5,941,836 A | 8/1999 | Friedman | |
| 6,032,530 A | 3/2000 | Hock | |

(Continued)

OTHER PUBLICATIONS

Micro Strain, Accelerometer Based Flexion Angle Inclinometer System, FAS-A Inclinometer, print from website, date unknown.

*Primary Examiner* — Anh V La
(74) *Attorney, Agent, or Firm* — Thomas E. Lees, LLC

(57) ABSTRACT

An assessment device is provided which allows for measurement of a position of interest, e.g., a body part, while a subject is in a functional position, such as may be required for the demands of an activity of interest without also requiring a lengthy setup time, tethered connection to other equipment external to the subject or tedious manual measurements. Moreover, an indicator such as an alarm or other output may be provided for receiving immediate, real time feedback, such as when a functional activity falls outside a tolerance or threshold.

29 Claims, 20 Drawing Sheets

U.S. PATENT DOCUMENTS

| | | |
|---|---|---|
| 6,059,576 A | 5/2000 | Brann |
| 6,129,686 A | 10/2000 | Friedman |
| 6,152,890 A | 11/2000 | Kupfer et al. |
| 6,426,719 B1 | 7/2002 | Nagareda et al. |
| 6,514,219 B1 | 2/2003 | Guimond et al. |
| 6,605,038 B1 | 8/2003 | Teller et al. |
| 6,703,939 B2 | 3/2004 | Lehrman et al. |
| 6,792,801 B2 | 9/2004 | Hoggan et al. |
| 6,821,257 B1 | 11/2004 | Jolley |
| 6,864,796 B2 | 3/2005 | Lehrman et al. |
| 7,095,331 B2 | 8/2006 | Lehrman et al. |
| 7,145,461 B2 | 12/2006 | Lehrman et al. |
| 7,264,554 B2 | 9/2007 | Bentley |
| 7,602,301 B1 * | 10/2009 | Stirling et al. ............ 340/573.1 |
| 7,843,351 B2 * | 11/2010 | Bourne et al. ............ 340/573.7 |
| 2002/0170193 A1 | 11/2002 | Townsend et al. |
| 2005/0046576 A1 | 3/2005 | Julian et al. |
| 2005/0126026 A1 | 6/2005 | Townsend et al. |
| 2005/0237209 A1 | 10/2005 | Van Dongen |
| 2006/0235642 A1 | 10/2006 | Vock et al. |
| 2007/0203433 A1 | 8/2007 | Murphy |

* cited by examiner

ASSESSMENT DEVICE

CROSS-REFERENCE TO RELATED APPLICATIONS

This application is a National Stage Application of International Application No. PCT/US2008/006104 titled ASSESSMENT DEVICE, filed May 14, 2008. This application also claims the benefit of U.S. Provisional Application No. 60/917,919 titled ASSESSMENT DEVICE, filed May 14, 2007. The disclosures of which are incorporated herein in their entirety.

BACKGROUND

The present invention relates to assessment devices and methods of using such assessment devices to monitor, detect, measure and/or analyze positions including postures, orientations and/or movements, including dynamic motion.

A conventional approach to measure the stability and control of the lower back of a subject requires the subject to lie supine over a pressure-detecting instrument such as an inflatable bladder that is attached to a pressure gauge. The subject then performs controlled movements with their arms and/or legs while learning to control the pressure being placed on the pressure-detecting instrument, which measures the forces applied to the lower back. In this regard, the subject receives feedback either by watching the pressure gauge or by receiving instructions provided by an observer, such as a trained clinician who is monitoring the activity. Moreover, under certain circumstances, the trained clinician interacting with the subject may utilize their hand as an alternative to a pressure gauge. Thus, the subject is trained to achieve better trunk stability, which results in lower back stress and improved movement patterns.

Other conventional techniques for measuring the stability and control of body parts of interest may rely on measuring distances associated with the body part of interest with a measuring tape or ruler, affixing a spirit level (bubble level) to the body part of interest and/or photographing or video recording the body part of interest and utilizing marker-based motion capture systems. However, these techniques are often labor-intensive, may be subject to significant error in measurements or interpretation or require the purchase of expensive equipment. A skilled technician and/or significant capital expenditure are also often necessary to use the above-described conventional techniques.

BRIEF SUMMARY

According to various aspects of the present invention, an assessment device for evaluating positions of interest comprises a sensing device configured to measure angles relative to at least one axis corresponding to a predefined sensor orientation and to output information indicative of detected angles with respect to each measured axis. For example, the sensing device may comprise an inclinometer that measures angles along one or more axes with respect to a sensor orientation defined by gravity or an artificial horizon.

The assessment device also comprises a controller for processing the information output by the sensing device and a plurality of input devices that are coupled to the controller. The input devices allow operating parameters of the assessment device to be set up and/or modified. The input devices comprise, for example, a threshold setting control for setting at least one user-selectable threshold parameter where each user-selectable threshold parameter is associated with a direction along a corresponding axis of interest. An axis of interest may be defined by the principle direction of motion to be evaluated. Still further, an input device such as a calibration setting control may be coupled to the controller for instigating an electronic calibration process. The assessment device still further comprises an output device that is coupled to the controller for selectively providing feedback to the user.

The controller is configured to determine a range of angles based upon at least one user-selected threshold parameter entered via the threshold setting control, where each threshold parameter is associated with a corresponding direction along a corresponding axis of interest within a user-defined orientation. The controller is further configured to implement an operational mode that monitors the output information of the sensing device. Angle measurements determined from the monitored output information of the sensing device are compared to the threshold values and the output device is initiated to convey information based at least upon the comparison of the determined angle measurements and the determined range of angles.

According to various aspects of the present invention, the user-defined orientation may not always correspond to the sensor orientation. Where it is determined that a tare operation is required or desired, e.g., where the user-defined orientation is different from the sensor orientation, the assessment device may be mechanically tared, electronically tared, or a combination of mechanical and electrical tare operations may be implemented, e.g., to perform coarse and fine calibrations.

According to various aspects of the present invention, the assessment device may provide a mechanical tare calibration capability. In this regard, a sensor component comprises a first member that is mountable to an object or subject of interest and a second member that is repositionable in at least one dimension with respect to the first member. The sensing device is rigidly secured to the second member. The first member of the sensor component is mountable to an object or subject of interest at a user-defined orientation with respect to a principle axis of a desired evaluation environment. The second member of the sensor component is correspondingly positioned and secured with respect to the first member of the sensor component so that the sensing device is substantially aligned to its predefined sensor orientation and a first axis of the sensing device substantially corresponds with the principle axis of the desired evaluation environment providing at least a coarse mechanical tare calibration.

Thus for example, where the sensing device comprises the above exemplary inclinometer, the first member can be positioned at any user defined angle and the second member and corresponding sensing device can be reoriented such that the inclinometer is maintained in an alignment substantially level to its intrinsic sensor orientation, e.g., an artificial horizon in the illustrative example.

According to further aspects of the present invention, the assessment device may further implement a fine tuning electronic tare calibration upon actuation of the calibration setting control. To implement the electronic tare, the controller reads the output information of the sensing device while the first member of the sensor component is held at the user-defined orientation. The output information read by the controller is then compared with an ideal position derived from the user-defined orientation to derive a calibration offset. The calibration offset is stored for use in position correction.

According to yet further aspects of the present invention, a mechanical tare and the corresponding first and second members may be unnecessary, such as where the sensor can measure three axes. For example, the controller may electronically calibrate during a tare operation by reading the output information of the sensing device while the sensing device is in a first known position. The controller further determines the orientation of the sensing device with respect to a reference orientation defining a first vector. The assessment device then reads the output information of the sensing device after the sensing device has been relocated to a second known position. The controller then determines the orientation of the sensing device relative to its reference orientation defining a second vector. The controller may then compute an orientation of the sensing device as it is moved through the desired position or range of motion based upon the first and second vectors.

According to further aspects of the present invention, a method of training using an assessment device for evaluating positions of interest comprises implementing a pre-training mode by connecting an assessment device to an object or subject of interest, where the assessment device comprises a sensor for measuring at least one angle. The pre-training mode further comprises capturing a set of data values that characterize maximum deviations of a desired motion or position with respect to at least one axis without providing user feedback, and saving the captured values as a baseline. Further, a training mode is implemented by repeating the position or motion, utilizing the assessment device to capture data values that characterize a range of the motion or position. Still further, the method comprises comparing the captured values to predetermined threshold values and providing feedback as to whether or not the motion or position breaches the threshold values to train the movement or position.

Still further, a post-training mode is implemented by utilizing the assessment device to capture data values that characterize maximum deviations of the desired motion or position with respect to at least one axis as without providing feedback, saving the data values as a post-training baseline and providing feedback as to whether the training is becoming more effective towards the desired motion or position based upon a comparison of the post-training baseline with the pre-training baseline.

DETAILED DESCRIPTION

According to various aspects of the present invention, an assessment device is provided that allows for the measurement of a position of interest, e.g., a body part, while a subject is in a functional position that may be static or part of a dynamic motion. The assessment device may also be utilized to measure a position of interest of an object such as a machine, tool, instrument, etc. In this regard, the assessment device may be utilized without requiring a lengthy setup time or tedious manual measurements. According to further aspects of the present invention, the assessment device may be utilized without also requiring significant amounts of bulky equipment external to the subject that would otherwise interfere with the assessment environment, which may define, simulate or otherwise represent a typical environment in which an activity of interest is performed.

According to further aspects of the present invention, an interface is provided on the assessment device that allows the user to program various aspects of the assessment device, e.g., by setting threshold limits, alarm parameters and other information related to assessment activities. Thus, for example, the assessment device may utilize one or more indicators to provide immediate, real time feedback, such as when a functional activity falls outside a pre-programmed tolerance or threshold.

Figure 1:
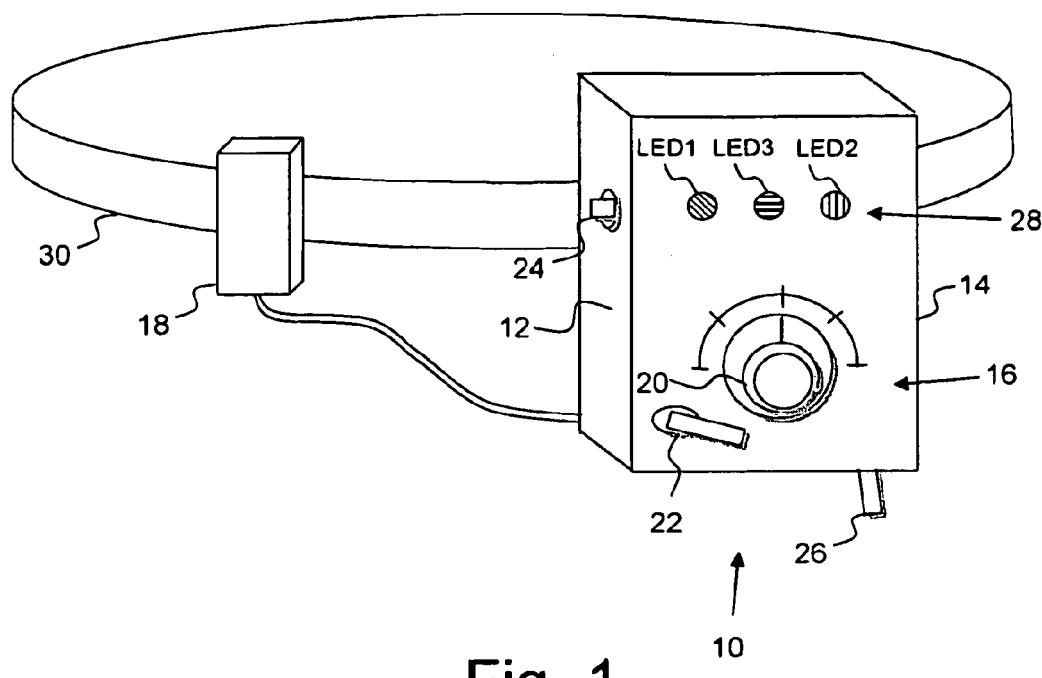
FIG. 1 is a representation of an assessment device according to aspects of the present invention.

Referring to FIG. 1, according to aspects of the present invention, an assessment device 10 comprises an integrated unit that includes operative controls and sensing capabilities built into a unitary housing 12. As illustrated, the housing 12 includes a front panel 14 having an interface 16 thereon for setting parameters of interest and/or otherwise operating the assessment device 10. Where at least some components of the assessment device 10 comprise active electronics, an optional battery pack 18 may be provided. The battery pack 18 or other suitable power source may alternatively be integrated into the housing 12 of the assessment device 10 thus eliminating the need for the external battery pack 18 and corresponding connecting arrangement, e.g., where size constraints or other considerations do not preclude a battery compartment within the housing 12.

As shown, the interface 16 includes a first control 20 that allows a user to select a suitable "threshold". The first control 20 is thus also referred to herein as a threshold setting control. As will be described in greater detail below, the assessment device 10 includes a sensing device (not shown in FIG. 1) that measures deviations along one or more (typically orthogonal) axes. Thus, the threshold sets a band in one or more directions relative to an associated axis of the sensing device. In the illustrative example, the first control 20 may comprise, for example, a multi-position rotary switch, encoder, etc. Moreover, indicia such as scale marking, values and other information may be associated with the first control 20 to facilitate precise operation.

According to various aspects of the present invention, a "normal" operating range may be defined by orienting the sensing device such that at least one axis aligns with a user-defined principle orientation. Positions or movements are considered normal so long as the sensor remains in the principle orientation or does not tilt beyond the tolerance set by the threshold parameter(s). Examples of setting the threshold are set out in greater detail herein. If the electronics detect a breach in the threshold setting, an alarm or other indicator can be triggered, providing real-time feedback to the user and/or others in the user's environment.

In certain applications, it may be desirable to focus on position or movement along a single axis or less than all of the axes available for measurement by the assessment device 10. In this regard, the assessment device 10 may further comprise a second control 22 for selecting which one (or more) axes are being processed by the assessment device 10. Thus, for example, assume the sensing device is implemented by a two axis inclinometer that is calibrated to measure deviations of orthogonal axis in a horizontal plane. The inclinometer may be oriented such that a first axis of the inclinometer aligns with a user-defined principle orientation, e.g., an anterior-posterior (front-back) orientation of a body part of a subject under evaluation. The assessment device 10 may thus be user selected by toggling the second control 22 to measure anterior-posterior (front-back) position or movement, or to measure medial-lateral (side-side) position or movement of the subject.

However, in an alternative implementation, both front-back and side-side may be simultaneously analyzed. Still further, the assessment device 10 may be oriented with respect to reference planes that are not horizontal as will be described in greater detail herein. Moreover, the threshold setting control 20 may be utilized to set a threshold in only a single direction along an associated axis, e.g., front only. Single-ended ranges may be useful, for example, when utilizing the assessment device 10 as a squat alarm or other similar application. The threshold setting control 20 may also set the same threshold in both directions relative to an associated axis, or the threshold control may set a different threshold for each direction relative to an associated axis. Moreover, threshold value(s) associated with each measured axis may be the same or different, as determined by the particular application and user adjustments.

A third control 24 may be utilized for setting a zero position. As will be described in greater detail below, this "zero" position corresponds to a user-defined principle orientation that may be determined relative to the horizontal or other suitable orientation, including in certain embodiments, a user selectable orientation that deviates significantly from the horizontal plane. The setting of the zero position is also referred to herein as a tare operation and is utilized to determine the mapping between the user-defined principle orientation and the intrinsic (absolute) sensor orientation, i.e., the intrinsic axis (or axes) of the associated sensing device. As such, the third control 24 is also referred to herein as a calibration setting control. For example, typical sensing devices such as inclinometers provide measurements relative a fixed, horizontal plane. A fourth control 26 may optionally be provided, e.g., as an on/off switch to allow a user to selectively turn the assessment device 10 on or off.

The interface also includes at least one output 28 that functions as an indicator. As shown, the output 28 comprises three light emitting diodes (LEDs). Two LEDs designated LED 1 and LED 2 respectively, may be utilized as threshold indicators. A third LED, designated LED 3 may be utilized to identify the current "zero" position.

According to various aspects of the present invention, a support 30 may be utilized to attach the assessment device 10 to a subject or object under evaluation. The support 30 may comprise any attachment device, examples of which include a hook and loop fastener such as Velcro, a rope, strap, a belt, clips, rubber tubing, a biocompatible adhesive, a neoprene sleeve, clamps, etc.

Thus, for example, the assessment device 10 may be attached to a subject, e.g., using the support 30. The assessment device 10 is positioned in a desired principle orientation and the third control is activated to tare the device to a reference zero position. The subject is then monitored by the assessment device 10 in a desired position, e.g., a posture, orientation and/or range of movement. If an angle measurement indicates that a selected axis of the sensor in the assessment device 10 deviates from its programmed threshold, a corresponding one of the LEDs will illuminate to designate a breach along a corresponding axis.

As noted above, the sensing device may comprise, for example, an inclinometer that measures angles of one or more axes. In this regard, the output of the inclinometer over its measurable range may appear to have a sine wave output response. The sine function is "fairly" linear near 0 degrees, so the assessment device may use the raw data from the inclinometer if the required precision allows. However, as the angle increases further from 0 degrees, the error increases. Thus, the error may be reduced by converting the voltages from the inclinometer using the arcsine function.

Thus, as used herein, the term "angle measurement" should be interpreted expansively to include not only actual angle values, e.g., expressed in degrees or radians, but also to include other values that represent or otherwise correspond to angle measurements. For example, for output voltages of an inclinometer corresponding to measured angles close to an intrinsic principle sensor orientation, e.g., level with respect to horizontal, a linear estimation of the angle can be assumed, thus allowing a simplification of processing. However, as the angle deviates further from the principle orientation, additional linearization processing of the output voltage of the inclinometer may be required to achieve a desired precision.

Moreover, angles may be expressed as encoded representations, etc., depending upon the particular implementation.

Figure 2:
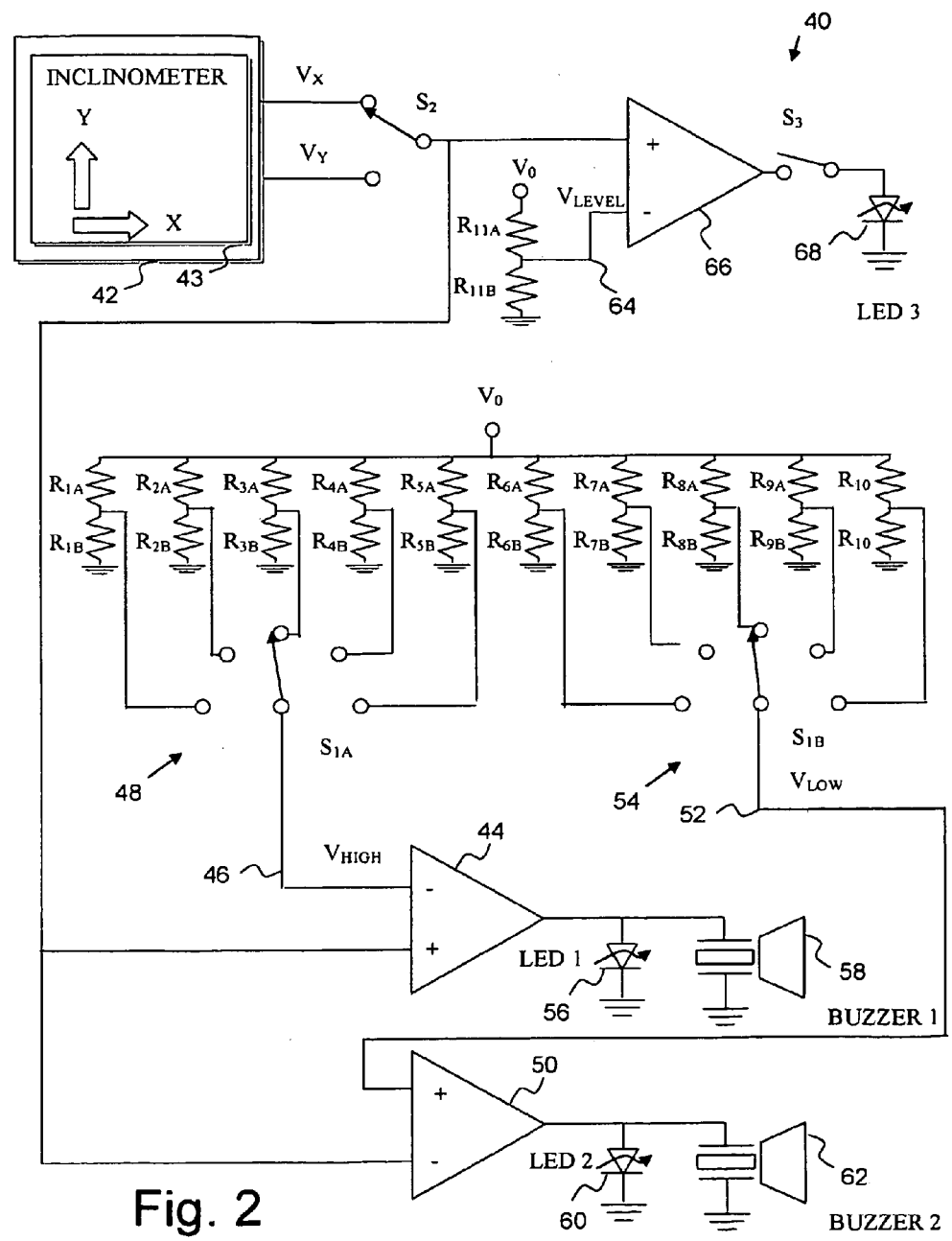
FIG. 2 is a schematic illustration of control electronics of an assessment device according to various aspects of the present invention.

Referring to FIG. 2, a simplified schematic of control electronics 40 is illustrated according to various aspects of the present invention. The control electronics 40 implements a controller that may be implemented for example, within the assessment device 10 of FIG. 1. As illustrated, a sensor 42 is provided for sensing one or more angles. Although the sensor 42 is described as being integrated into the housing 12 of the assessment device 10 of FIG. 1, the sensor 42 may be individually packaged and electronically coupled to the other control electronics of the assessment device 10 either wired or wirelessly as will be described in greater detail herein. In an exemplary configuration, the sensor 42 comprises a measuring arrangement including a sensing device, e.g., an inclinometer 43 such as an SCA100T inclinometer by VTI Technologies of Dearborn Mich., USA. Other inclinometers or other forms of angle measuring devices may be utilized. However, the SCA100T is a convenient inclinometer as it interfaces to both analog as well as digital systems.

The sensing device, inclinometer 43, is configured to measure angles relative to at least one axis of a predefined sensor orientation and to output information indicative of detected angles with respect to each measured axis. For example, the inclinometer 43 provides an output, e.g., a ratiometric analog voltage output that corresponds to the angle of the inclinometer along two axes. As shown, VX designates a voltage output along the X-axis of the inclinometer and VY designates a voltage output along the Y-axis of the inclinometer. The X and Y axis are measured with regard to a predefined sensor orientation defined by an artificial horizontal plane. If the application only requires one axis at a time, an optional switch S2 may be provided to select one of the two available axes. For example, the switch S2 may correspond to the second switch 22 described with reference to FIG. 1.

As shown, the output of the sensor 42 is coupled to the "+" input of a first comparator 44. The "−" input of the first comparator 44 is tied to a first reference signal 46 determined by first reference signal circuitry 48 that designates a first one of the threshold boundaries relative to a designated zero position, described below. Similarly, the output of the sensor 42 is further coupled to the "−" input of a second comparator 50. The "+" input of the second comparator is coupled a second reference signal 52 determined by second reference signal circuitry 54 that designates a second one of the threshold boundaries relative to the designated zero position.

The first and second reference signals 46, 52 represent known angles of inclination of the sensor 42, and may be controlled by a single switch S1, such as a double pole 5 throw switch (the poles designated by S1A, S1B respectively), which is also shown as the threshold setting control 20 in FIG. 1. The 2-pole, 5-throw (2P5T) rotary switch allows a user to select from a set of high/low threshold voltages to compare to inclinometer voltage output.

Each section of the switch S1, i.e., S1A and S1B, includes a pole corresponding to the first and second reference signals respectively, which couples to one of five throws. For each section, S1A and S1B, each throw is programmed to a different reference value. For example, as shown, resistors R1A and R1B form a voltage divider with respect to voltage Vo, e.g., a power supply voltage or other suitable reference, to set a first reference value. As shown, each throw is programmed to a desired reference level in a manner analogous to that described with reference to the first throw. Thus, in general, resistors RiA, RiB (where i is a number 1-10 as shown in the figure) represent resistors used in voltage divider circuits composed of two series resistors connecting between power and ground. These create a reference voltage equivalent to $V0*[RiB/(RiA,+RiB)]$.

The illustrated 2-pole, 5-throw rotary switch configuration thus selects which set of two voltage dividers to be compared with the inclinometer output. Once the assessment device 10 has been calibrated, the user can use the rotary switch to select the two threshold voltages corresponding to a change in position of the inclinometer of plus or minus a default angle. As an example, the assessment device 10 may be programmed, or otherwise configured such that the above 2-pole, 5-throw switch allows 5 choices, such as 2, 4, 6, 8, 10 degrees of deviation from a default angle. Alternatively, any type of input device may be used to designate any number of options.

Although shown for sake of illustration as voltage divider networks, the reference signals derived by the first reference signal circuitry 48 and second reference signal circuitry 54 can be programmed using any number of alternative arrangements, including the use of potentiometers, encoders, digital controls, etc. Also, while it is convenient to express the various threshold reference signals in terms of angles of deviation, other units of measure may alternatively be utilized.

Figure 3:
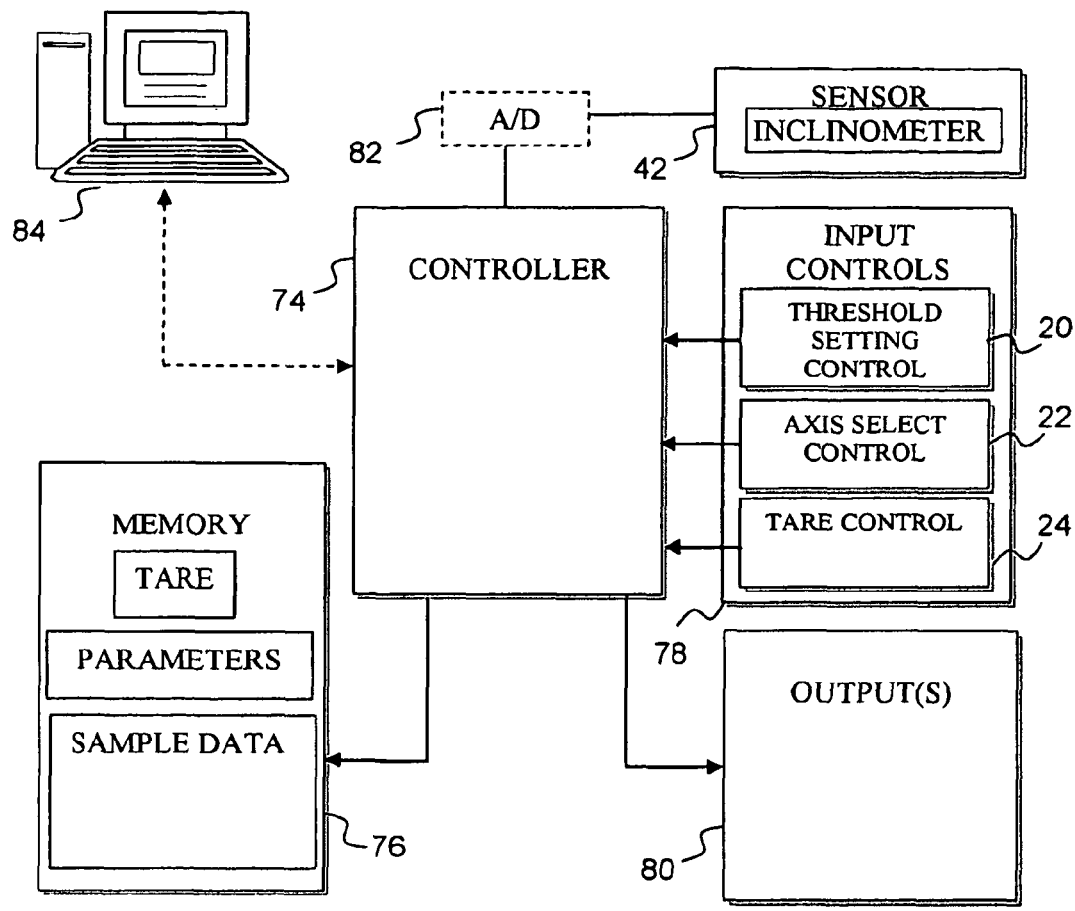
FIG. 3 is a schematic illustration of a digital implementation of an assessment device according to various aspects of the present invention.

The output of the first comparator 44 is active if the inclinometer signal exceeds the first reference signal 46 and may be used to trigger an output device 56, e.g., LED 1 as shown in FIG. 1, and/or any other suitable output device, such as buzzer 58, also designated as BUZZER 1, etc. As such, the first comparator 44 sets an upper threshold value. Similarly, the output of the second comparator 50 is active if the inclinometer falls below the second reference signal and may be used to trigger an output device 60, e.g., LED 2 as shown in FIG. 3, and/or any other suitable output device, such as a buzzer 62, also designated BUZZER 2, etc. As such, the second comparator 50 sets the lower threshold value. Thus, resistors R1A/B-R5A/B of the first reference signal circuitry 48 correspond to voltage dividers creating the upper threshold voltages to compare inclinometer voltage to (VHIGH). Similarly, resistors R6A/B-R10A/B of the second reference signal circuitry 54 correspond to voltage dividers creating the lower threshold voltages to compare inclinometer voltage to (VLOW).

The first and second reference signals 46, 52 thus set upper and lower bounds relative to the zero position. In many practical applications of the assessment device 10, the goal is to stabilize a body part in a specific (static) position. The user should be able to maintain the static position of that body part even while dynamically moving other body parts. As such, symmetrical thresholds are likely to be utilized. However, asymmetrical thresholds that are programmed to any desired value may be set if the application requires as much, e.g., by using one or more switches or encoders that provide independent control of the high and low threshold values.

As noted above, switch S2 is used to select one axis of the two axis outputs from the sensor 42. As such, the user can use switch S2, to toggle, for example, between front-back assessments or side-side assessments, etc. However, if both inclinometer outputs are to be simultaneously monitored, then the first and second comparators 44, 50 and corresponding reference signal circuitry 46, 52 can be duplicated for each axis, with the same or different threshold value options.

The output of the sensor 42 may also be compared to a third reference signal 64, designated as Vlevel by a third comparator 66. The output of the third comparator 66 may be coupled to an output device 68, e.g., LED 3 as described above with reference to FIG. 1, via switch S3. The Vlevel signal 66 is shown as a being created by a voltage divider consisting of the series arrangement of resistors R11A and R11B. However, any desired technique can be used to set Vlevel, including the use of a potentiometer or other suitable means. The Vlevel signal 64 can be used, for example to identify the "zero" position of the sensor 42, which may be fixed with reference to the horizontal or vertical. Alternatively, the zero position may be user selectable as will be described in greater detail herein.

The Vlevel signal 64 corresponds to the voltage output of the R11A/B voltage divider, which is calibrated to correspond, e.g., to be equal to, the inclinometer value at it's zero value. For example, where it is desirable to set the zero value level with horizon, R11A may be set equal to R11B. S3 may comprise, for example, a momentary single pole, single throw switch to display if inclinometer voltage exceeds Vlevel. Thus LED3 turns on when S3 is pushed and inclinometer voltage exceeds Vlevel.

The comparators may be implemented, for example, using LM339 comparators. Under this arrangement, an output of the comparator=V0 (or supply rail) if input V+>V−. Otherwise, the output of the comparator remains at ground, i.e., the output=0. Thus, when the inclinometer voltage exceeds the upper threshold voltage, an alarm, such as LED1 is turned on. Further, Buzzer1, if provided, turns on. Buzzer1 may be configured to emit a first tone, e.g., a high tone when turned on. Similarly, when the inclinometer voltage falls below the lower threshold voltage, an alarm, such as LED2 is turned on. Further, Buzzer2, if provided, turns on. Buzzer2 may be configured to emit a second tone that is different from the first tone of Buzzer1, e.g., a low tone when turned on.

Moreover, the inclinometer described with reference to FIG. 2 is capable of measurements in two orthogonal directions. In this regard, the specific applications will determine the sophistication of the required sensor. For example, where the motion to be measured is unconstrained, six linear accelerometers may be utilized, e.g., to identify three linear and three angular accelerations. If the anticipated system is constrained in one or more directions, then the number of accelerometers or other sensing devices may be reduced.

Thus, the controller, e.g., control electronics 40, is configured to determine a range of angles based upon at least one user-selected threshold parameter entered via the threshold setting control and the user-defined orientation. For example, the user selects a threshold range using the switch S1 to select how far the angle can deviate from the user defined orientation. The controller is also configured to implement an operational mode that monitors the output information of the sensing device and determines angle measurements from the monitored output information of the sensing device, e.g., via signals VX and VY, compares the determined angle measurements to the determined range of angles and initiates the output device 56, 58, 60, 62 to convey information based upon the comparison of the determined angle measurements and the determined range of angles.

Referring to FIG. 3, according to various aspects of the present invention, the control electronics may be implemented digitally. For example, as shown the control electronics may comprise a controller 74 such as a microprocessor, microcontroller or other form of digital circuitry coupled to the sensor 42. The control electronics may further include storage 76, such as a memory for storing the various parameters and other information associated with the assessment device 10. For example, the storage may preserve input control parameters, tare information, output control parameters, sample data collected during use and other relevant information, examples of which are set out in greater detail herein. Inputs 78 are coupled to the controller 74. The inputs may comprise for example, the threshold setting control 20, the axis select control 22, the calibration setting control 24 and other inputs described throughout this specification. The inputs 78 may be implemented with devices such as buttons, switches, encoders and Similarly, output device(s) 80 are coupled to the controller 74. For example, a rotary encoder may be used to program one or more thresholds by allowing the user to select any number of degrees of deviation. Still further, a potentiometer or other device may be utilized as an alternative to a switch, e.g., by coupling the potentiometer to an analog to digital converter and sampling the potentiometer value. Still further, a keypad may be used to key in a desired deviation to any desired degree of precision, as the application dictates. The entered values may then be stored in appropriate registers or other appropriate locations in memory.

The output device(s) 80 may comprise for example, buzzers, LEDs, a series of LED or bar meters, a display such as a seven segment display that provides for one or more digits, tone generators, vibrators/vibrator motors for generating tactile feedback, and other outputs along with their corresponding driver circuitry as required for the specific implementation.

Outputs may also encompass integration with other devices or appliances. For example, the assessment device 10 may integrate with existing appliances such as portable music players, treadmills or other exercise equipment.

In this regard, the controller 74 implements the functions of reading the angle measurements from the sensor 42, e.g., by reading analog or digital output signals from an inclinometer and comparing the sensor readings against pre-programmed parameters, e.g., threshold values. For example, the controller 74 may implement the functionality of the circuitry described with reference to FIG. 2. Moreover, because the controller is implemented digitally, advanced functionality may also be implemented. For example, the controller 74 may process multiple thresholds, perform necessary computations such as reference voltage to angle computations and perform other necessary conversions and processing, e.g., for filtering and/or converting the output(s) of the sensor into more accurate values. For example, the controller 74 may implement smoothing or averaging of collected angle samples. The processor 74 may also throw out outlier values, perform windowing or other processing techniques, depending upon the application. Additionally, the controller 74 may perform data collection, logging and archival, etc.

The ability to record data further allows the ability to record peak/average, standard deviation of multiple individual trials and other measures.

It is likely that the output of the sensor 42, e.g., an inclinometer, is an analog signal. Thus, an optional analog to digital (A/D) conversion 82 may be utilized to convert an analog output of the inclinometer to a digital signal for processing by the controller 74. In this regard, many microcontrollers have built in A/D capabilities so that an external converter may be unnecessary. Moreover, the inclinometer may provide a digital output that can be directly interfaced by the controller 74. The controller 74 may also be configured physically separated from the sensor, either using wired or wireless connections.

Still further, the controller 74 can interact with controls on the interface to adjust parameters of use, perform functions such as storing which thresholds have been selected by the user, turning on/off or otherwise creating feedback cues, such as the outputs generated when a breach is detected.

As the feature set increases, the display on the assessment device may be required to become more sophisticated, or the assessment device 10 may include an interface that allows the assessment device 10 to be temporarily connected to a processing device such as a computer 84. As such, software may be used to program the assessment device 10. Using a software interface, the user can make all the choices at a software front end, trigger a programming or downloading of the new parameters, unplug the programming connection, and use the assessment device un-tethered to the computer.

Figure 4:
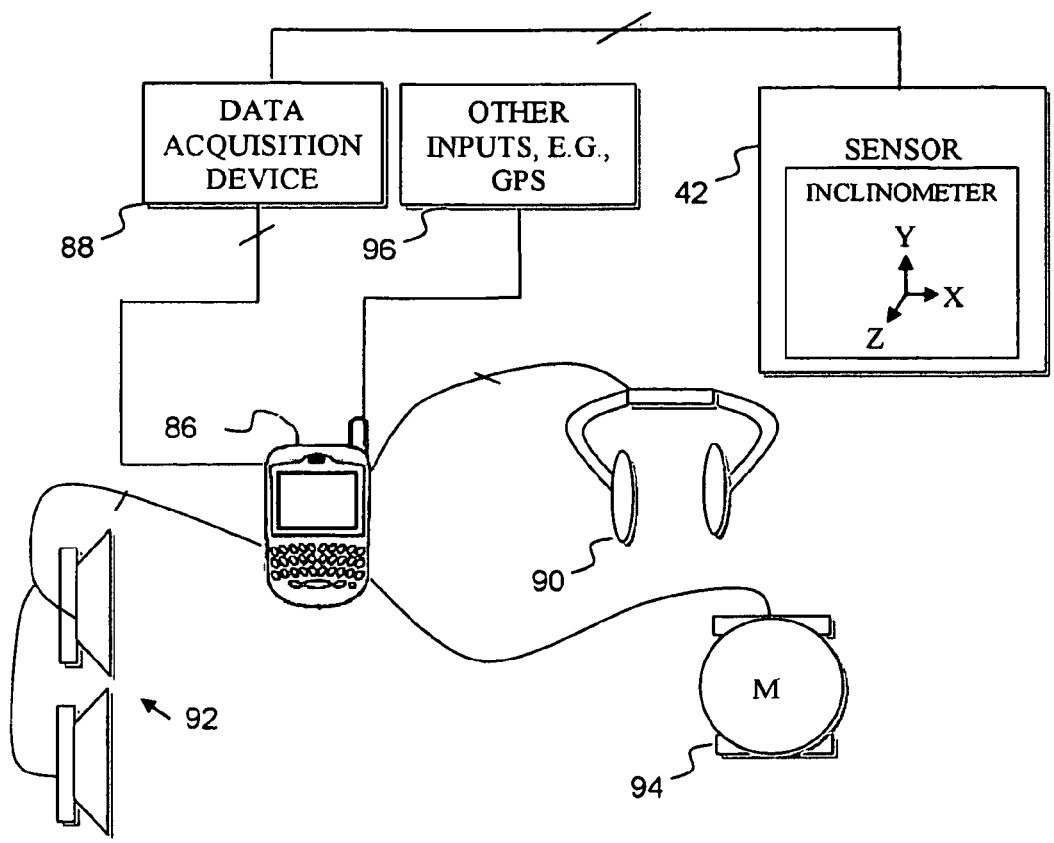
FIG. 4 is a block diagram of an assessment device incorporating a hand-held computing device according to various aspects of the present invention.

Referring to FIG. 4, according to still further aspects of the present invention, the controller 74, storage 76, inputs 78 and/or outputs 80 may be implemented by a hand-held computing device 86 and corresponding software.

For example, the processing device may be implemented by an HP iPaq 2490 PDA by the Hewlett Packard Company of Palo Alto Calif., USA. Other exemplary portable computing devices may comprise, for example, a personal digital assistant (PDA), laptop, palm, a cellular telephone with computing capability such as an iPhone or iPod by Apple of Cupertino, Calif., or other portable pervasive computing devices.

An optional data acquisition device 88 may be required to interface the sensor 42 to the portable computing device 86. In this regard, the above illustrative HP iPaq includes a compact flash slot that enables the PDA to be used with commercial data acquisition devices that fit in the compact flash slot. For example, a CF-6004 by National Instruments of Austin Tex., USA may be plugged into the compact flash slot to provide an interface between the sensor 74 and software executing on the PDA. The software for controlling the CF-6004 may comprise one or more applications created utilizing the Labview development environment (IDE), also by National Instruments. The inclinometer may comprise for example, an Analog Devices ADXL 322 by Analog Devices of Norwood, Mass., USA. With this configuration, the PDA can power the inclinometer via the compact flash slot and/or data acquisition card so as to not require an external power source. Alternatively, the inclinometer may be integrated with a transceiver, e.g., a Bluetooth capable device or any other standardized or proprietary wireless technologies. Under this arrangement, there is no need to wire the inclinometer to the portable computing device 86 (or data acquisition device 88).

In the arrangement of FIG. 4, the sensor 42 may be positioned and arranged independently of the associated controls of the assessment device. As such, the tare operation (if performed) is implemented with regard to the sensor 42 and not the assessment device housing (portable computing device 86) per se.

As noted above, the assessment device 10 may utilize any number of outputs as indicators. For example, the assessment device 10, e.g., via the portable computing device 86, controller 74 (see FIG. 3), etc., may be configured to provide features such as feedback modalities, e.g., the ability to provide positive feedback (feedback that the activity is being done correctly) as well as negative feedback (feedback that the activity is being performed incorrectly). Still further, feedback may only be provided if a breach of a threshold is detected (threshold feedback).

The assessment device 10 may also provide "proportional feedback". That is, feedback changes proportionally as deviations are detected from an ideal position. As a few illustrative examples, a graduated metering of threshold breaches may be implemented. For example, the output, e.g., one or more lights may get brighter depending upon the magnitude of the breach or deviation from an ideal position. Still further, changes of color of a screen/lights/LEDs etc., may be used to indicate the degree of deviation. For example, blue may be used to designate a deviation of 0 degrees, green a deviation of 2 degrees, yellow a deviation of 4 degrees, orange a deviation of 6 degrees, red a deviation of 8 degrees and violet a deviation of 10 degrees. A line of LEDs may also be used where the number of LEDs that light up indicate the deviation or a gradation of deviation. Still further, a picture may become fainter/more snowy as deviation increases.

As additional examples, an alarm may get louder depending upon the magnitude of the breach or deviation from an ideal position. Additional examples of audible alarms may include a frequency of tone that changes as deviation changes. This may allow the user to differentiate direction. As further examples, volume may change as deviation changes, a pulse frequency may change as deviation changes, music may get fainter as deviation increases and/or music may receive dropouts with increasing duration/frequency as deviation increases. Also, a sound generator may be utilized to generate complex, potentially changing audible cues. All of these above techniques could be used for positive feedback or negative feedback.

As still further examples, tactile responses may include having the vibration pulses get closer together as deviation changes, having the vibration pulses get stronger as deviation changes, etc. As yet another example, electrostimulation may be utilized to designate a breach of the threshold. Pulses stimulate muscle activity as deviation exceeds threshold and changes. For example, a dead band of no stimulation may be provided within the bound of the threshold values. However, an increasing frequency of pulses of increasing intensity may be utilized as deviation increases. As another example, neuromuscular re-education may be implemented by stimulating muscle activation in muscles that promote desired positioning.

As yet a further example, instead of programming a single threshold relative to the zero reference, the assessment device may comprise an output device for multiple thresholds. For example, a status LED may be used to indicate which thresholds (if any) have been crossed.

With graded alarms an onset of likely breach can be detected and/or predicted and the user may receive a warning, e.g., of the potential for the breach. For example, two sets of thresholds may be provided. A first set of threshold values defines a "dead band" where the user is holding the desired position optimally. A second set of threshold values defines a maximum threshold. There may also be advantages to not giving a warning, because providing proportional feedback makes the user's own sensory system less necessary, which may inhibit their own proprioception.

As yet further examples, the assessment device 10 may be able to emit distinct audible tones, visual cues, or tactile cues so that the user can more readily interpret the output of the assessment device 10. In this regard, different tones, intensities, patterns or other techniques can be used to distinguish one or more threshold breaches. Additionally, the tones may further vary to designate the breach along two or more axes simultaneously.

As a few illustrative examples, the assessment device 10 may be provided with dual stereo audio outputs to allow the user to hear audible tones, e.g., through quadraphonic headphones 90 and/or a plurality of speakers 92. As yet further exemplary outputs, tactile cues may be generated, such as in the form of vibrations from a motor 94, e.g., similar to those generated by a mobile phone or pager. For example, a vibration may be generated when the position of the device exceeds a threshold. This vibration stays on as long as the threshold is exceeded. As another example, vibration pulses may be generated when the position of the assessment device exceeds an initial threshold, where the pulses get closer together as the device gets farther and farther past the threshold. Still further, vibrations may be generated by the device itself, by a tethered remote device that is also affixed to the body part of interest or another body part on the subject that is more sensitive to tactile stimuli. Although several exemplary outputs are illustrated, a particular implementation will dictate the most appropriate one or more outputs utilized.

While using the assessment device for training, a user may be interested in counting the number of breaches during an interval, such as to obtain an intermediate measure of progress. Accordingly, a counter or other suitable structures may be included to count the number of times a threshold is breached.

In addition to various outputs, the assessment device 10 according to various aspects of the present invention may include other inputs 96, such as global positioning (GPS) or other sensor inputs. GPS or similar tracking technologies allow for extended range of motion testing. For example, when monitoring runners, cyclists, rowers, roller bladers, skiers, snowboarders, motorcyclists, etc., it may be that the number or severity of threshold breaches occurs after reaching a certain distance, speed, etc. Further, threshold breaches may change as a function of endurance, etc. Thus, the GPS signals can be tracked and logged in a manner that allows the assessment device 10 to correlate its sensor measurements and breaches with position, speed, distance, time and other parameters measured by the additional input(s) 96.

Figure 5:
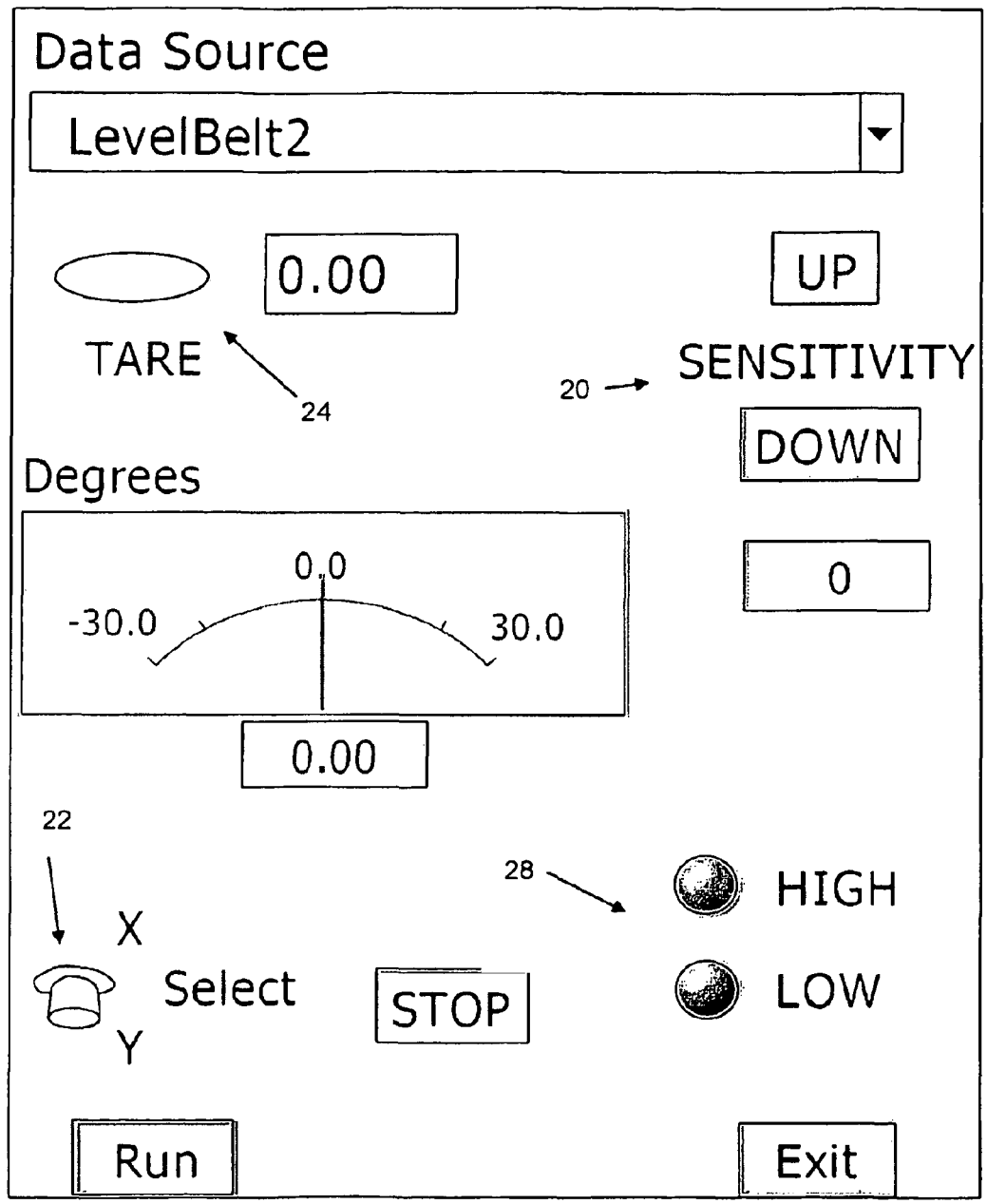
FIG. 5 is an exemplary screen shot of the virtual controls of an assessment device implemented using a portable computing device according to aspects of the present invention.

It is possible to combine cues to multiple senses. Once a microcontroller or other suitable control electronics is incorporated that can generate all of these different sensory feedback options, the user may be allowed to choose which options in any combination to use.

Where the assessment device is implemented using a portable computing device or other suitable processor and display, the inputs and outputs may include virtual components, e.g., virtual buttons, boxes, and other controls that appear on a display screen. Referring to FIG. 5, a screen shot illustrates an exemplary virtual interface for an assessment device 10, e.g., as illustrated in FIG. 4. The screen shot illustrates the threshold setting control 20, the axis selection control 22 and the calibration setting (tare) control 24 implemented as virtual controls on the display screen. Also illustrated is a gauge that shows an actual measure of the measured angle and controls for starting and stopping the application. Still further, outputs 28 are implemented as virtual LEDs.

With reference to FIGS. 1-5 generally, the controls may comprise any combination of switches, rotary switches, buttons, encoders, potentiometers or other contact or contactless technologies for interfacing with the electronics of the assessment device. Similarly, the outputs may be virtual and/or hardware implemented. For example, virtual LEDs may be implemented on the display screen. Still further, where the assessment device 10 includes a display screen, the output may take the form of messages, icons, dynamically changing images, visual gauge or meter displays of the computed angle of deviation from the programmed zero orientation, etc. Moreover, parameters such as a threshold can be varied by the user, e.g., in stepped amounts such as by using a rotary switch, or in a continuously variable manner, such as by using potentiometers or similar variable technologies.

According to aspects of the present invention, the output device(s) may comprise audible, visual, tactile, olfactory, etc., cues to indicate the state of the assessment device. Also, multiple different output arrangements may be used together or separately. For example, visual cues via the LEDs can be augmented by audible signals produced by buzzers, etc., which are controlled by corresponding control electronics of the assessment device 10.

Where visual output devices are utilized, such as virtual or discrete LEDs or other lights, different colors can be used to further distinguish which threshold has been breached. This may allow, for example, the user to be able to more readily interpret the output of the assessment device. Moreover, where a visual output device including a screen is utilized, such as a PDA, graphics may be used to further enable the user to interpret the output. For example, an image of an person in a position of exaggerated anterior pelvic tilt can be used to correspond to the anterior tilt threshold being crossed.

In analog implementations, the tare voltage may be stored in a capacitor with a Sample-and-Hold circuit or the tare value may be stored in memory if digital capabilities are utilized. Moreover, when using digital implementations, the audible cues may comprise digitally generated tones or waves in software which are sent to a speaker, or the sound may be generated by powering solid-state buzzers.

Figure 6:
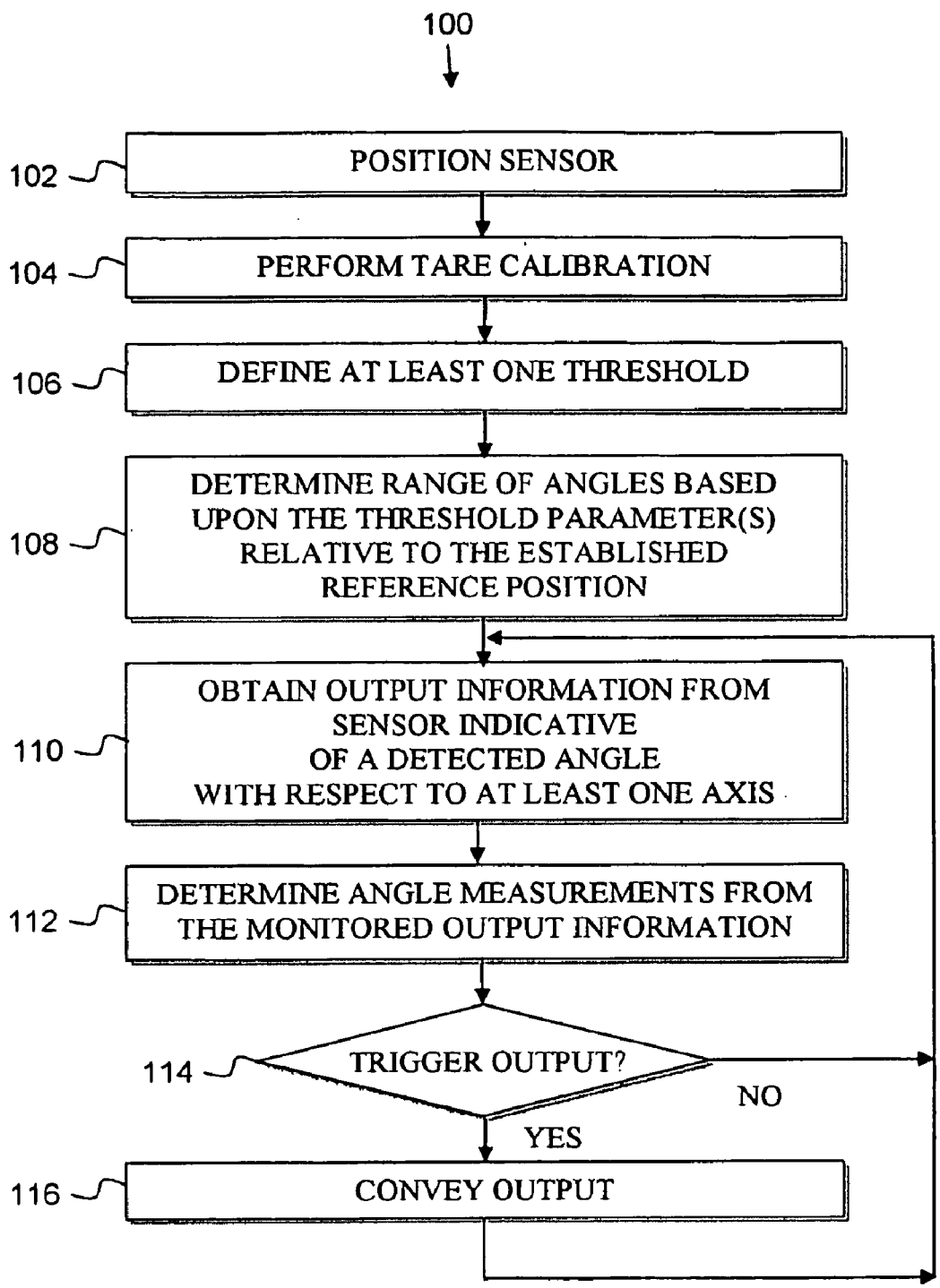
FIG. 6 is a flow chart illustrating a method of utilizing an assessment device according to aspects of the present invention.

Referring to FIG. 6, a flow chart 100 illustrates a method of utilizing an assessment device according to aspects of the present invention. The sensor 42 of the assessment device is positioned at 102 to a user-defined principle orientation. If the sensor is integrated in a single housing with the interface, e.g., as illustrated in FIG. 1, then the entire assessment device is positioned in a desired orientation. If the sensor 42 is separated, e.g., via wired connection or wireless connection from the interface, then only the sensor component 42 need be positioned in the desired orientation. A Tare calibration is performed at 104. As will be described in greater detail herein, the tare calibration may be performed mechanically, electrically or via a combination or mechanically and electrically. As will be described in greater detail herein, the tare operation is utilized to determine the mapping between a user-defined principle orientation and the intrinsic (absolute) sensor orientation, i.e., the intrinsic axis (or axes) of the associated sensing device.

Also, at least one threshold is defined at 106. For example, for each axis that is to be evaluated, one or more thresholds may be established, e.g., using the threshold setting control 20, entering threshold parameters(s) into the controller 74, entering the threshold parameters into a software entry form in the portable computing device 86, etc. With the threshold(s) defined, the assessment device can determine a range of angles that define "normal" operation based upon the threshold parameters relative to an established reference orientation defined as part of the tare calibration. For example, if the tare calibration at 104 is purely mechanical, or if the reference orientation is already defined with respect to horizontal, then the range of angles that define "normal" operation are the threshold ranges themselves. Thus, the determination at 108 may be conceptual and/or optional, depending upon the reference orientation. Alternatively, where tare calibration includes an electronic component, then the thresholds are relative offsets from the established reference orientation.

The assessment device obtains output information from the sensor indicative of a detected angle with respect to at least one axis at 110 and determines angle measurements from the monitored output information at 112. As a few illustrative examples, if the sensor comprises an inclinometer, the sensor may output a voltage that corresponds to the measured angle. If the angle is close to the reference orientation, e.g., within a few degrees, then a linear approximation of the angle may provide appropriate precision. However, if the angle deviates significantly, then a linear approximation may or may not yield the desired precision. Under this arrangement, the controller may be required to convert the voltage output to a corresponding angle using an arcsine function. Still further, the inclinometer may output the angle for direct interpretation.

A determination is made at 114 as to whether an output should be triggered, or if some other action should be taken, e.g., a data value recorded, a log or event record generated, etc. For example, if a threshold has been exceeded, then it may be desirable to generate a tone, sound a buzzer, illuminate an LED, provide a message, etc.

If a determination is made not to trigger an output at 114, then the control then loops back to 110 to obtain additional information until the assessment process is terminated. If a determination is made to trigger an output at 114, then the appropriate output is conveyed at 116. The control then loops back to 110 to obtain additional information until the assessment process is terminated.

Once the assessment device is made operational, the subject or object is put through an evaluation, e.g., maintaining a posture, going through a range of motions, etc. During the evaluation, the assessment device determines the range of angles experienced by the sensor, which are compared to the threshold parameters.

In an exemplary application of use, the assessment device 10 and/or just the sensor component 42 of the assessment device 10 may be affixed to a subject, e.g., about the subject's iliac crest using the support 30. The first control 20 may be utilized to dial in a desired threshold either before or after attaching the assessment device to the subject. For example, it may be desirable to train a subject to exhibit a (functional) posture or movement such that a body part of interest does not deviate from a desired range, e.g., +/−2 degrees from a default orientation, e.g., relative to the horizontal. As such, the threshold setting control 20 is set to a setting corresponding to a threshold of 2 degrees or any other desired angle. The assessment device is aligned to a principle orientation and if necessary, e.g., where the principle orientation is not aligned to the horizontal, the third (tare) control 24 is activated to calibrate the sensor.

The subject then practices the posture or movement. If the activity (posture or movement) deviates from the desired activity orientation by an amount that exceeds the threshold amount, e.g., 2 degrees from the tared orientation in this example, an appropriate one of the output devices may indicate the breach. For example, if the breach of threshold exceeds the desired orientation in a first direction, e.g., to the left, a first one of the LEDs, e.g., LED 1, will illuminate and if the breach of threshold exceeds the desired orientation in a second direction, e.g., to the right, a second one the LEDs, e.g., LED 2 will illuminate. Other orientations, angles and parameters in general may alternatively be implemented.

According to yet another aspect of the present invention, methods of providing feedback on positioning and/or training are provided. Positive or negative feedback to positioning could come in the forms of visual, audible, tactile, and/or smell cues as noted in greater detail above. Further, feedback can be either continuously varying or based on crossing one or more, e.g., a series, of thresholds. Visual cues can come in the form of lights that turn on or off in response to correct or incorrect positioning. These lights may be on the device itself or on a remote device that is either tethered or wirelessly connected to the sensing device.

Audible cues can come in several different forms. As several illustrative examples, tones of different frequencies that turn on or off in response to correct or incorrect positioning. A first frequency may be used to indicate tilt in each direction, so that a subject or technician knows which tilt is occurring. The threshold for when the tone turns on/off may optionally be adjusted between several pre-selected values, and is described in more detail herein. As yet further examples, continuously variable audible feedback may be implemented using a tone frequency that changes based on the angle of the device. The frequency may change in steps or grades based on exceeding different levels of threshold, or the frequency may be infinitely-variable.

Continuously variable audible feedback may also be implemented using a pulsed tone that increases or decreases in frequency as the angle of the device changes. The pulse frequency may change in steps or grades based on exceeding different levels of threshold, or it may be infinitely variable. Audible cues may be generated either within the device itself or through a remote sub-device that is either tethered to the main device or connected wirelessly. When generated through the remote sub-device, the cues may have directionality to them to indicate the direction of tilt, similar to surround sound in a home theater or movie theater sound system.

The assessment device may for example, emit four distinct audible tones, visual cues, or tactile cues so that it can be used to assess front-back and side-side position simultaneously. Different frequency tones, beats, patterns, etc., may thus be used for the four directions in a two axis device so the user can differentiate between them. Where lights such as LEDs are used, lights may be positioned in four different parts of the user's field of view so that the user can differentiate the output of the assessment device. As yet a further example, four pager-motor type vibrators may be positioned at different places on the body part or other part of the body to allow the user to differentiate between the four directions sensed by the inclinometer.

As yet a further example, it may be possible to utilize smell cues when the position of the device either exceeds a threshold or is within a threshold. These smell cues may be either unpleasant (negative feedback) or pleasant (positive feedback).

The way in which a person moves or positions themselves can vary greatly based on which muscles are being recruited for the movement pattern or positioning. Movement and positioning is most often a learned pattern of selective neuromuscular recruitment which is influenced by the body's proprioception or awareness in space. Often, poor movement patterns and positions expose individual to undue stress to their musculoskeletal structures and risk for injury.

Various aspects of the present invention allow for measuring, evaluating, analyzing, classifying, training for improved performance, rehabilitating, etc., a body part of interest in a functional position. Body parts of interest include any body parts for which assessing and training correct positioning is important, such as for preventing or treating injury, pain, or discomfort. Examples of which may include the foot, shank, thigh, pelvis, lumbar, lower torso, upper torso, shoulders, upper arms, forearms, hands, neck and head.

Threshold levels for feedback may be established during calibration of the assessment device 10, such as by placing the sensor 42 at known angles relative to the horizon. This calibration may be performed using any available means, including but not limited to using a spirit level, protractor, and tiltable platform or other technique to identify when the sensor 42 is approximately in the desired orientation. The sensor may then be secured in the desired orientation and the sensor angle measurement(s) are read and recorded. The threshold voltages are then programmed or registered into the assessment device electronics. For example, as illustrated in FIG. 2, the predetermined threshold values may be programmed using voltage dividers (resistors placed in series connected to the power and ground terminals of the power supply), stored in memory as illustrated in FIGS. 3, 4, etc.

As noted above, the measurement arrangement within the assessment device may comprise an inclinometer, such as the above-described SCA100T dual-axis 1-g inclinometer, or other inclination measurement device, which outputs a signal, e.g., a voltage, which is a function of the angle of the inclinometer, typically relative to the horizon. The default orientation of such commercial devices is usually with respect to the horizon or gravity, depending upon the measured axis. According to further aspects of the present invention, the user-defined principle orientation designating the zero orientation may be determined mechanically, electrically, or using a combination of mechanical and electrical approaches regardless of the intrinsic sensor orientation, e.g., to the horizontal.

Figure 7:
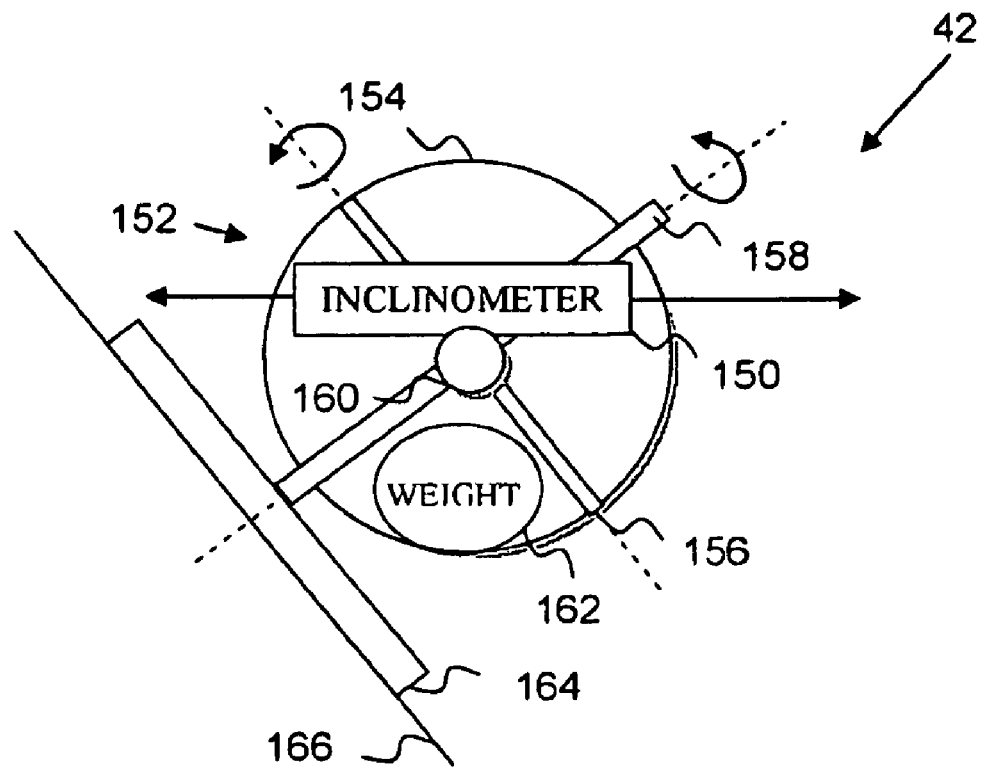
FIG. 7 is an illustration of a sensor including a gimbal for performing a mechanical tare operation according to aspects of the present invention.

Referring to FIG. 7, as an illustrative example, the sensor component 42 may comprise a first member that is mountable to an object or subject of interest, and a second member that is repositionable in at least one dimension with respect to the first member. For example, the sensor component 42 may include a sensing device such as an inclinometer 150 that is supported by and or rigidly secured to a second member such as a gimbal 152. For example, a sensing device such as a 2-axis inclinometer 150 may be supported by a 2-axis gimbal 152 that is utilized to reorient the inclinometer 150 with respect to a first member, e.g., the housing of the assessment device 10 if integrated with the interface as illustrated in FIG. 1, or with respect to the sensor component housing, e.g., where the sensor is remote from the assessment device interface as illustrated in FIG. 3 or 4. In this regard, the readings of the inclinometer are relative deviations from a calibrated reference (the intrinsic sensor orientation) and not absolute angle measurements of the sensor housing itself.

As illustrated, a main core component 154 for supporting the inclinometer 150 may be generally spherical in shape, with a groove 156 around an equator of the main core component 154. A ring 158 surrounds the core, with a thumbscrew 160 that fits into the groove. The core 154 can rotate around the axis of the thumbscrew, or rotate around an axis perpendicular to the plane of the groove. The core 154 is weighted 162 such that when the thumbscrew is loosened, the core 154 rotates until it finds its balance, with the weighted part at the bottom.

The surrounding ring 158 may also include a first member such as an attached plate 164. The plate 164 can be affixed to a surface 166 of interest, e.g., a body part of interest using biocompatible adhesive, hook-and-loop fasteners, or any other means. Still further, the plate 164 may be attached to equipment or other objects under evaluation.

In this method, the power switch and threshold select button(s) may be placed on the surface of the core along an axis perpendicular to the plane of the groove if the interface is integrated with the sensor. Alternatively, the interface may be wired or wirelessly connected to the core. Once the device is placed in position, it is considered tared.

Thus, the sensing device is substantially aligned to its predefined sensor orientation, e.g., an artificial horizontal plane, despite the plate 164 being oriented at some angle different from the artificial plane. Moreover, to facilitate measurements, a first axis of the sensing device may be aligned to substantially correspond with the principle axis of the desired evaluation environment providing at least a coarse mechanical tare calibration.

Figure 8:
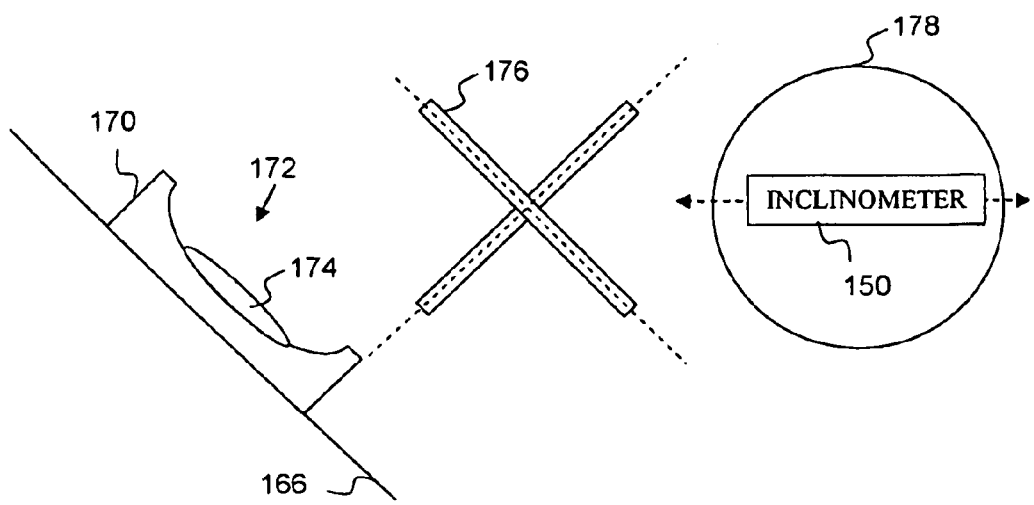
FIG. 8 is an illustration of a sensor including first and second members that cooperate for performing a mechanical tare operation according to aspects of the present invention.

Referring to FIG. 8, according to yet further aspects of the present invention, the first member may be implemented as a cuff 170 with a dish-shaped receptacle 172 that may be affixed to a surface 166, e.g., the body part of interest or an object of interest. The dish-shaped receptacle 172 has a temporary attachment arrangement 174, e.g., hook-and-loop fasteners on its concave surface. A harness 176 may further be provided that includes a securement arrangement that cooperates with the attachment arrangement 174 to secure the sensor device to the cuff 170.

As illustrated, the exemplary harness 176 includes a pair of orthogonal straps. For example, two hook and loop fastening straps may be oriented about two principle axis, e.g., equator and north/south pole for vertical alignment or any other orientation.

The sensor device may be integrated into a ball shaped housing component 178 that includes sufficient markings, indicia or other manner of determining the orientation of the inclinometer therein. For example, the housing component 178 may have an equator marked on its circumference, with the power switch and threshold select buttons at the equivalent of the north pole if the interface is integrated with the sensor. As another example, where the housing component 178 couples to a separate interface, e.g., via a wired or wireless interface, then the equator may be marked on the housing 178, or the user may know the orientation of the housing 178, e.g., if the housing 178 is wired to the interface based upon orientation of the wires extending from the housing 178.

The device is affixed to the receptacle by the user so that the equator lies in the plane that the primary motion of the body part occurs in. If two planes are to be measured, either can be chosen as the primary plane. Once the device is placed in position, it is considered tared.

The housing component 178 is oriented so that the inclinometer is aligned with to its default sensor orientation, typically with regard to the horizontal, and an axis is aligned generally towards the direction of primary motion. The harness 176 is positioned over the housing component 178 and the harness 176 and housing component 178 are temporarily secured to the cuff 170.

Figure 9:
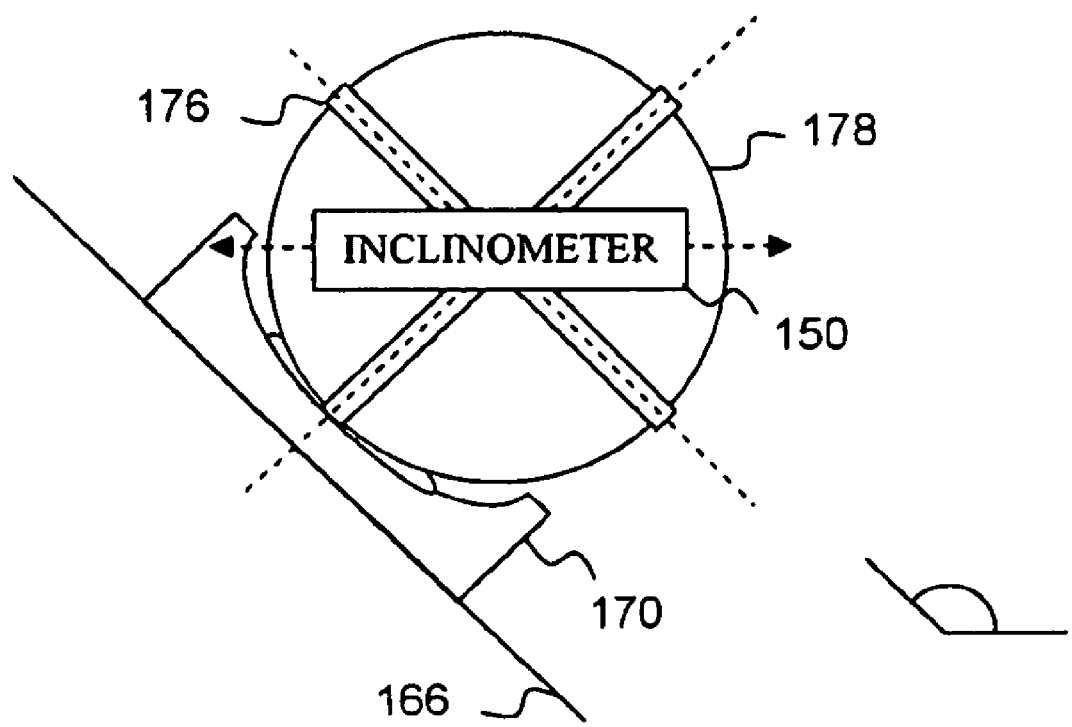
FIG. 9 is an illustration of the sensor of FIG. 8 secured into an operative position for evaluation according to aspects of the present invention.

Referring to FIG. 9, the harness 176 is illustrated attached to the housing component 178 and the harness is further temporarily secured to the cuff 170. Notably, the cuff 170 is oriented in a user defined orientation, e.g., 45 degrees relative to the horizontal. Under this arrangement, the inclinometer measures angles relative to a first axis, e.g., to the horizontal. Thus, in order to display the actual angle of the position or motion, the assessment device adds the measured angle to the difference in angles between the cuff 170 and the inclinometer within the housing 178. Notably, this approach may allow the inclinometer to measure near its default axis, thus potentially eliminating the need for implementing calculations such as arcsine conversions to accurately determine the absolute angle of the cuff.

Figure 10:
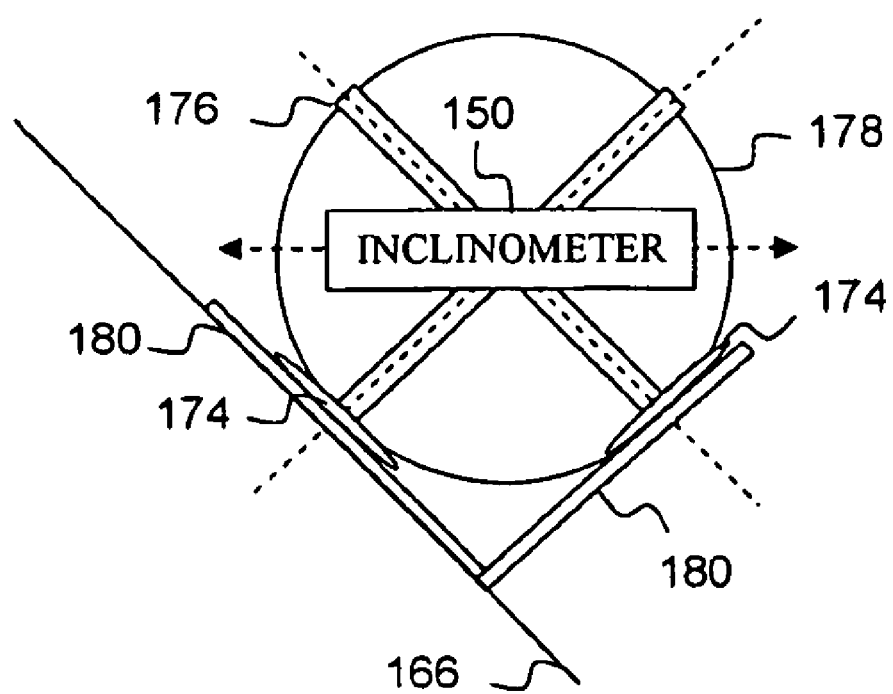
FIG. 10 is an illustration of yet another sensor including first and second members that cooperate for performing a mechanical tare operation according to aspects of the present invention.

Referring to FIG. 10, the cuff 170 may be replaced by other configurations such as a generally "L" shaped right angle bracket 180. The bracket includes a fastening arrangement, such as hook and loop on orthogonal surfaces of the bracket for receiving the harness. The L-shaped bracket 180 provides two orthogonal surfaces that may be aligned with corresponding orthogonal members of the harness 176 thus facilitating quick and intuitive alignment of the harness 176 and ball housing with the bracket 180. A user slips the harness 176 over the ball housing. The user further knows the orientation of the inclinometer within the ball housing, e.g., by virtue of appropriate indicia, the exit point of wires where attached to the ball housing, etc. As such, the principle axis of the inclinometer can be aligned to a first orientation, e.g., the horizontal plane, and the housing can be oriented to another, different orientation. As an alternative to the harness 176, the housing component 178 may be covered in a material that temporarily secures to the attachment arrangement 174 of the cuff 170.

Because the device assumes that the signals from the two axes of the inclinometer are independent from each other when they are in reality rigidly connected to one another, errors can result from incorrect mechanical placement of the device or moving the device through large angles. These errors are characterized by overestimation of the angles. However, when used with a defined maximum threshold value, e.g., of 10°, such as may be achieved when using a mechanical adjustment as part of the tare procedure, mechanical placement of the inclinometer device can be off by as much as 20° relative to the horizontal while maintaining a relatively low error rate, e.g., of less than 1.5°.

According to aspects of the present invention, a tare may be implemented electronically. The user may affix the assessment device to the body part of interest and orient the device appropriately. For example, the user may place the body part in its desired position and press a tare control, e.g., the tare button 24 on the assessment device 10. When the tare button 24 is pressed, the sensor 42 is read. For example, the voltages of the two axes of the inclinometer are read, e.g., using a microcontroller or other suitable control electronics. The microprocessor or other suitable control electronics then stores the measurements from the sensor 42. Thus for example, where the sensor 42 comprises a 2-axis inclinometer, the assessment device 10 may store the voltage outputs from the inclinometer, angle measurements computed from the voltage measurements that were read out, or some other representation of the sensor outputs 42.

The assessment device may also perform the necessary offset processing to convert the threshold angles selected by the user to a corresponding reference signal for data processing by the assessment device.

For example, the microcontroller may utilize a suitable conversion, e.g., using an arcsine function, to calculate the angle of the device in each axis and stores those values. After calibration, the assessment device may be used. While the device is in use, the microcontroller repeatedly reads the voltages of the two axes, converts those voltages to angles, e.g., using an arcsine function, and subtracts the stored values to get the "tared" angle values. These tared angle values are compared to the programmed threshold values, e.g., as selected by the user, to determine whether feedback or an alarm should be given. Thus, as an illustrative example, assume that angle is desired to be measured along a single axis. Further, assume that the desired orientation is 10 degrees relative to horizontal. Still further, assume that the threshold values set for the exemplary implementation are +3 degrees and −2 degrees. The sensor 42 is placed at 10 degrees and the tare button 24 is pressed. This stores the 10 degree desired orientation.

During operation, the angle of the sensor 42 is repeatedly measured. 10 degrees is subtracted out from the measured angle to get a normalized angle measurement and that normalized angle measurement is compared to the threshold values. Thus, during evaluation, if the sensor 42 measures, for example, an angle of 18 degrees, the assessment device converts the absolute measurement to a relative measurement value by subtracting out the tare value of 10 degrees to derive a relative angle measurement of 8 degrees. This relative value is compared against the threshold parameters, in this example, +3 degrees and −2 degrees. Since 8 degrees exceeds the upper limit, an indication is provided that identifies the upper threshold as being exceeded, e.g., by illuminating an LED. Further, if the assessment device 10 includes a display screen, then any number display techniques may be implemented. For example, the display may be updated with a visual metaphor such as an image representing the angle of inclination or other graphic illustration of the assessment device, e.g., in a dashboard style display. Moreover, the computed or measured value of the angle may be displayed if the assessment device has a suitable display.

A separate mechanical arrangement for orienting the inclinometer may not be necessary under all circumstances. For example, a tri-axial version of the sensor may provide enough data to allow vector arithmetic to be utilized to discover the orientation of the sensor in three-dimensional space. Such an approach may further allow, for example, a measurement of tilt around two axes.

With a conventional two-axis inclinometer, cross talk can cause errors in the angle measurements. Cross talk worsens as the angle increases. A solution to cross-talk is to constrain the system such that one axis of the inclinometer aligns with the principle axis to be measured.

However, according to various aspects of the present invention, ambiguity in space is eliminated by utilizing three axes. For example, a sensing device may be configured to measure angles relative to at least three orthogonal axes of a reference orientation, e.g., with respect to gravity or an artificial horizon. The sensing device outputs information indicative of detected angles with respect to each measured axis.

In this regard, the sensor is placed in an operative position and the orientation of the sensor is discovered relative to a reference, e.g., gravity. Thus for example, the controller may read the output information of the sensing device while the sensing device is in a first known position, determine the orientation of the sensing device relative to its reference orientation and define a first vector relative to the first known position and reference orientation.

The sensor is moved to a second position, and again, the orientation of the sensor is discovered with regard to the reference. Thus for example, the controller may read the output information of the sensing device while the sensing device is in a second known position, determine the orientation of the sensing device relative to its reference orientation and define a second vector relative to the second known position and reference orientation.

As such, the system now knows two vectors in space and vector arithmetic may be implemented to track movement. Thus, the controller may compute an orientation of the sensing device based upon the first and second vectors and determine a calibration offset based upon the determined orientation and the reference orientation. Under this arrangement, cross-talk is eliminated, even where the angle has transitioned significantly from the reference. Thus, the tri-axial sensor arrangement allows a tare operation to be performed in any direction with no preferred orientation of the sensor. Moreover, alignment of the primary plane is performed functionally.

Thus, the controller may be configured to implement an operational mode that monitors the output information of the sensing device, determines angle measurements from the monitored output information of the sensing device, compares the determined angle measurements to the determined range of angles and initiates the output device to convey information based upon the comparison of the determined angle measurements, the determined range of angles and the derived calibration offset to determine, for example, whether a breach of a threshold has occurred.

Figure 11:
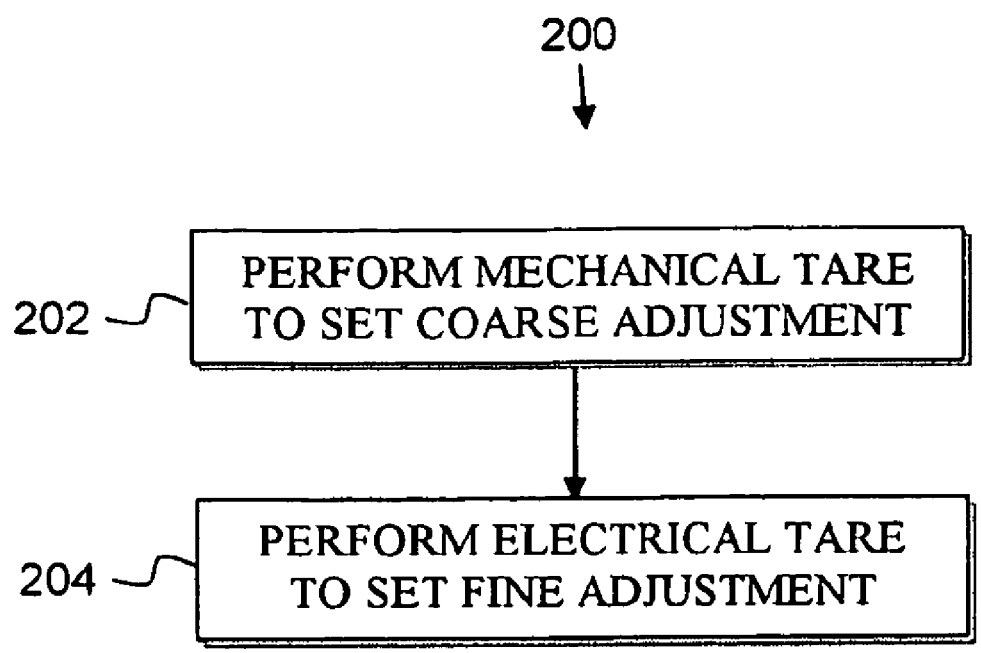
FIG. 11 is a flow chart illustrating a method for implementing a tare operation according to aspects of the present invention.

Referring to FIG. 11, a method 120 of setting a zero orientation comprises performing a mechanical tare at 122 to set a coarse adjustment. An electrical tare is performed at 124 for setting a fine adjustment and is thus referred to herein as a fine tuning electrical tare calibration. For example, the assessment device may be mechanically placed in a rough approximation of the proper position. Then electrical taring of the device is then performed, e.g., upon actuation of the calibration setting control 24, for fine corrections to the mechanical adjustment. Such an approach provides the convenience of simplifying the computations required by the electronics, especially where the threshold angles are relatively close to the zero orientation.

As an illustrative example, with reference to FIGS. 7-10, a fine tuning calibration may be performed by reading the output information of the sensing device while the first member of the sensor component is held at the user-defined orientation. The output information read out by the controller is then compared with an ideal position derived from the predefined orientation of the sensing device to derive a calibration offset. This calibration offset may be stored in memory and may be used to correct angle measurements read by the controller. As such, the controller may be further configured to initiate the output device to convey information based upon the comparison of the determined angle measurements, the determined range of angles and the derived calibration offset.

Practical considerations, such as the range of the inclinometer being utilized, may affect the manner in which the tare function is implemented. Still further, the voltage to angle conversion may require attention when implementing an electronic tare solution. For example, given the ratiometric output of the inclinometer, angle measurements close to 0 degrees may likely be implemented using straight line computations. However, as the angle increases, as is likely the case when implementing the tare function electronically, arcsine conversion may be necessary to minimize conversion error.

Figure 12:
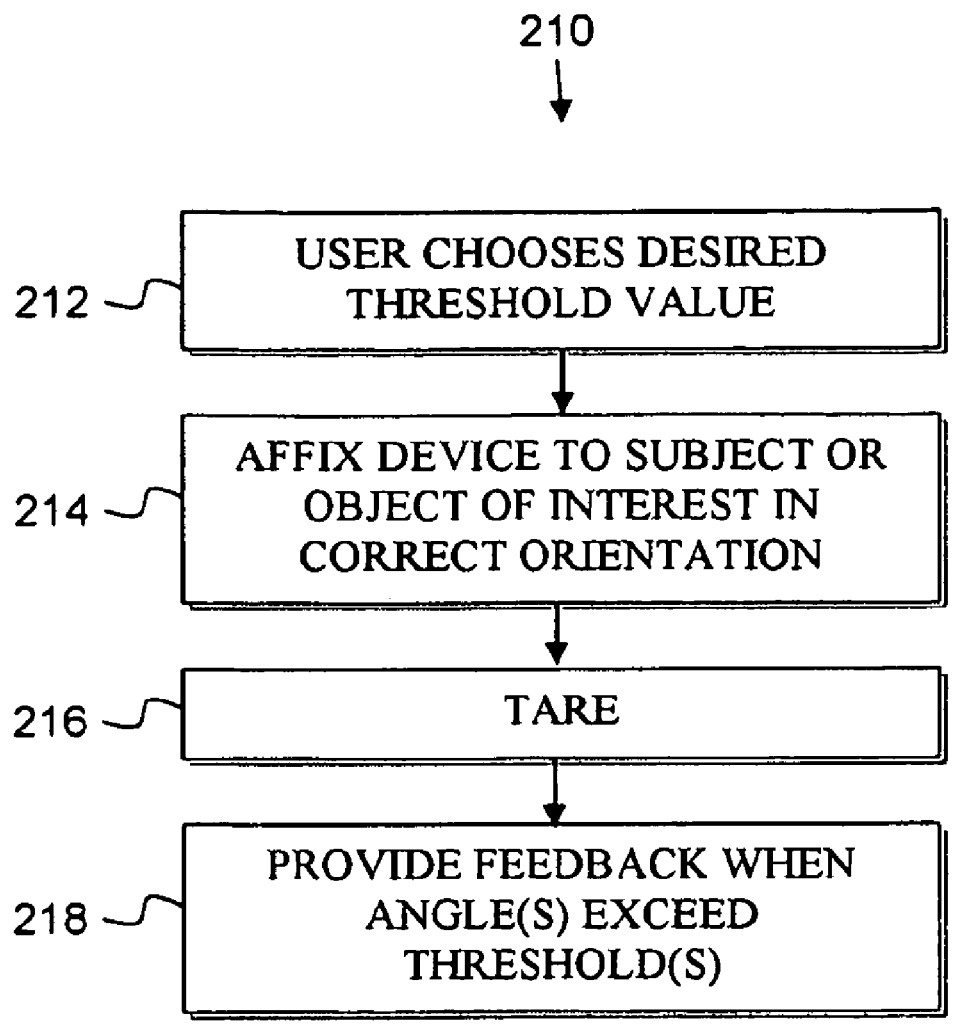
FIG. 12 is a flow chart illustrating a method for using the assessment device according to aspects of the present invention.

Referring to FIG. 12, a method 210 of using an assessment device according to an aspect of the present invention is illustrated. The user chooses a desired threshold value at 212. The user affixes the assessment device to the body part of interest in a correct orientation at 214. The user presses the TARE control (threshold setting control) at 216 and the assessment device calibrates itself. The assessment device provides feedback when an angle exceeds the user selected threshold(s) at 218.

Figure 13:
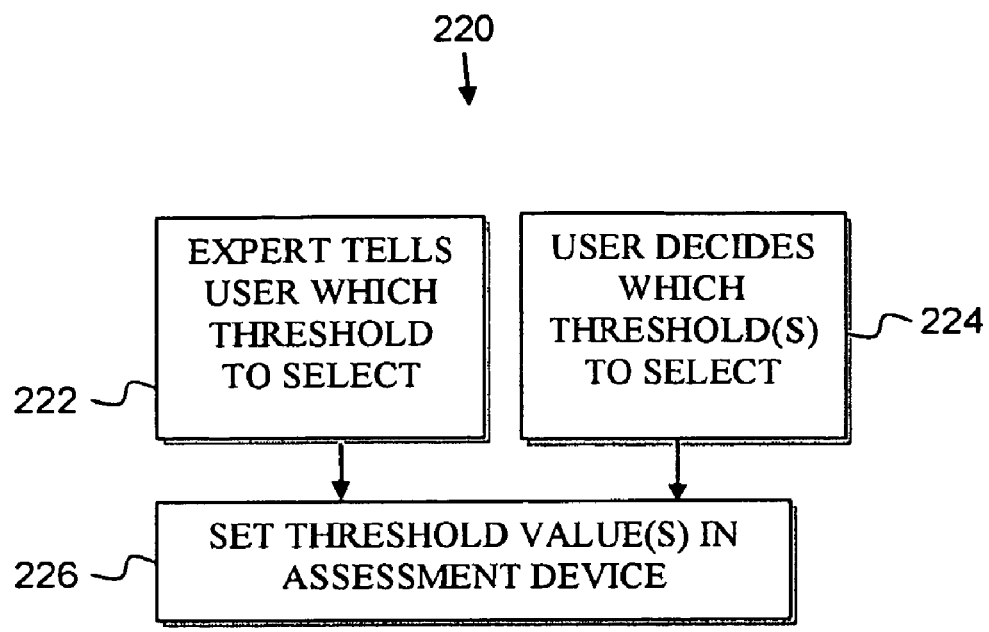
FIG. 13 is a flow chart illustrating a method of setting a threshold for using the assessment device according to aspects of the present invention.

Referring to FIG. 13, an exemplary method 220 of allowing a user to choose a desired threshold according to an aspect of the present invention is illustrated. Either an expert tells the user at 222 which threshold to use or the user decides at 224 which threshold to use based upon past experience or trial and error. For example, a novice may start off at the largest threshold and work towards the smallest threshold. The user turns the threshold knob 20, e.g., as illustrated in FIG. 1, or otherwise uses an interface control to select the desired threshold at 226. For example, in a digital interface, the user may push a button to cycle through options until the desired threshold range is identified.

Figure 14:
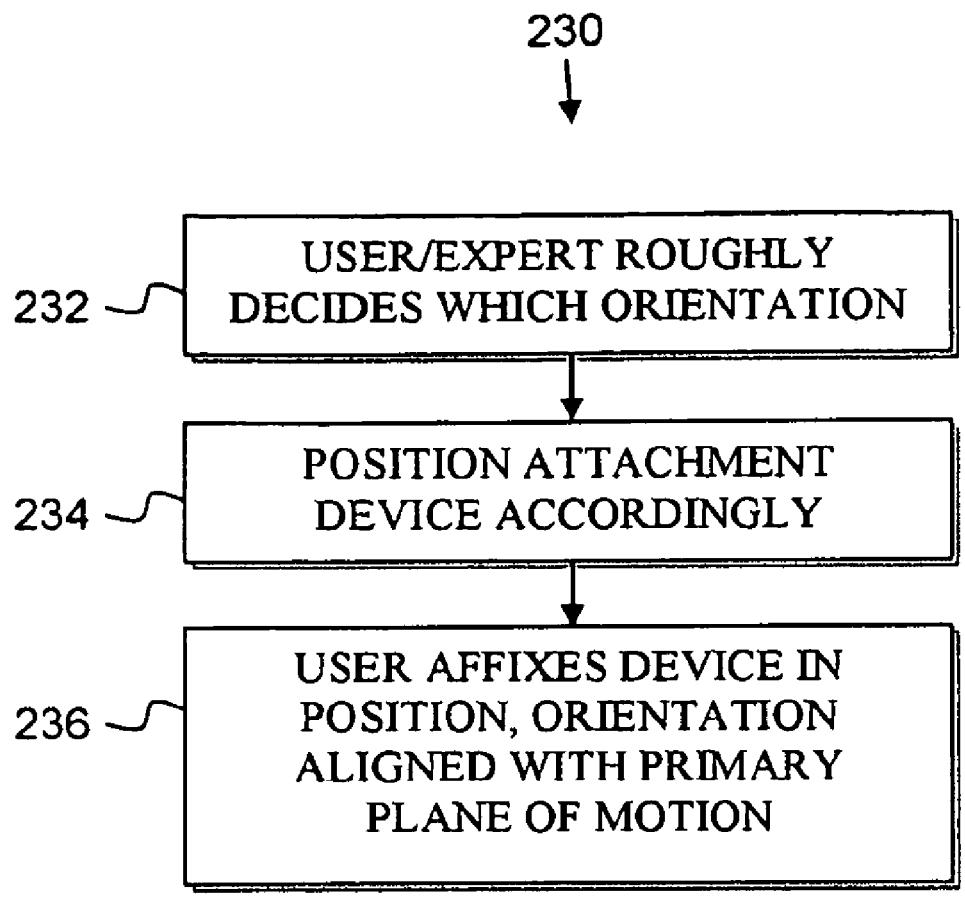
FIG. 14 is a flow chart illustrating a method of positioning the assessment device for use according to aspects of the present invention.

Referring to FIG. 14, an exemplary method 230 of allowing the user to affix the assessment device or sensor component to the body part of interest in a correct orientation according to an aspect of the present invention is illustrated. The user or an expert roughly decides which orientation is best for a given activity at 232. The assessment device or sensor component thereof is positioned at an attachment point accordingly at 234. The user affixes the device in the proper position and an orientation is aligned with a primary plane of motion at 236.

Figure 15:
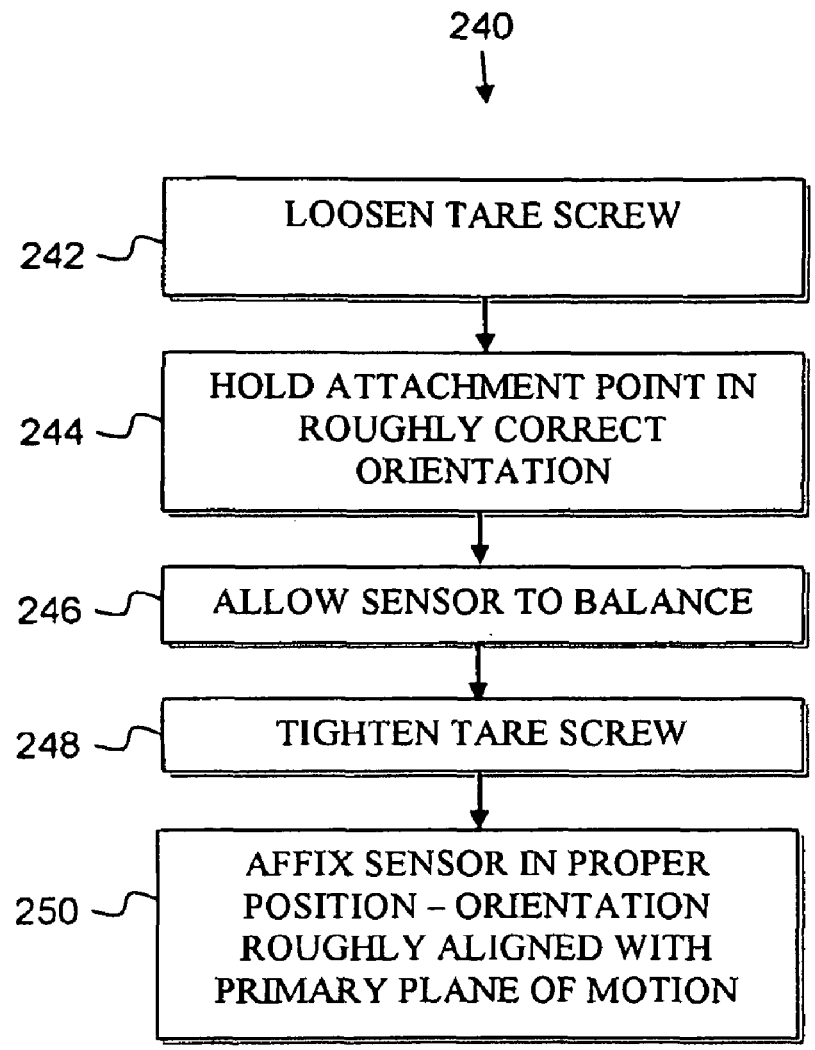
FIG. 15 is a flow chart illustrating a method of implementing a mechanical tare to calibrate an assessment device according to aspects of the present invention.

Referring to FIG. 15, an exemplary method 240 of allowing the user to affix the assessment device or sensor component thereof to the body part of interest in a correct orientation according to another aspect of the present invention is illustrated. This method may be used, for example, with the first mechanical arrangement for implementing tare as described above with reference to FIG. 7. The user loosens a TARE screw at 242, e.g., that fits into a groove about a core having a ring that surrounds the core, with a thumbscrew that fits into the groove as described above. The user holds an attachment point in and roughly corrects the orientation of the assessment device at 244. The device is allowed to balance itself at 246. Once balanced, the user tightens the TARE screw at 248. The user then affixes the device in a proper position and orientation at 250 such that the device is roughly aligned with a primary plane of movement.

Figure 16:
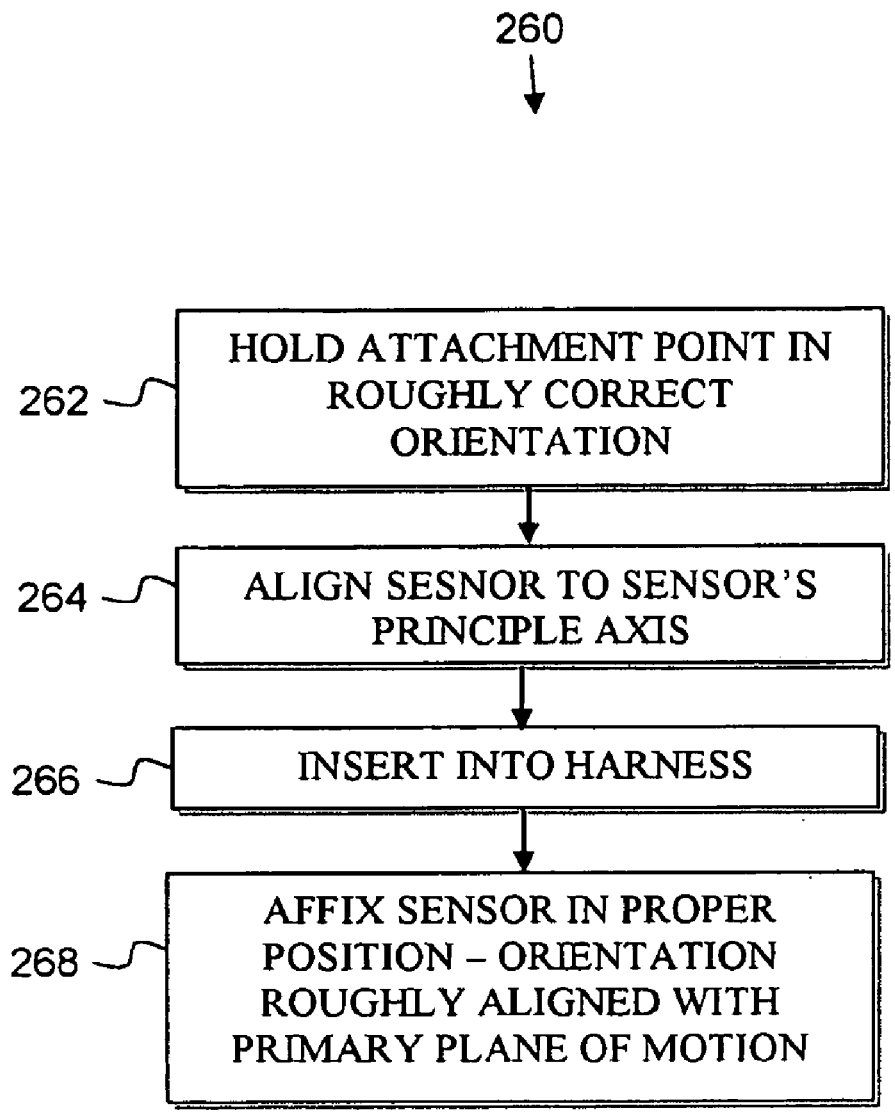
FIG. 16 is a flow chart illustrating a method of implementing a mechanical tare to calibrate an assessment device according to aspects of the present invention.

Referring to FIG. 16, as an alternative to using a mechanical gimbal, a, method 260 illustrates an exemplary approach to mechanical tare, for example, with the mechanical arrangements as described above with reference to FIGS. 8-10. The user holds the attachment point roughly in the correct orientation at 262. This may comprise setting the attachment point at any angle, including angles that are not horizontal. The sensor is aligned to the sensor's principle axis, e.g., relative to the horizon at 264. The sensor is slipped into a harness at 266 and the sensor is affixed in a proper position/orientation roughly aligned with the primary plane of motion.

Figure 17:
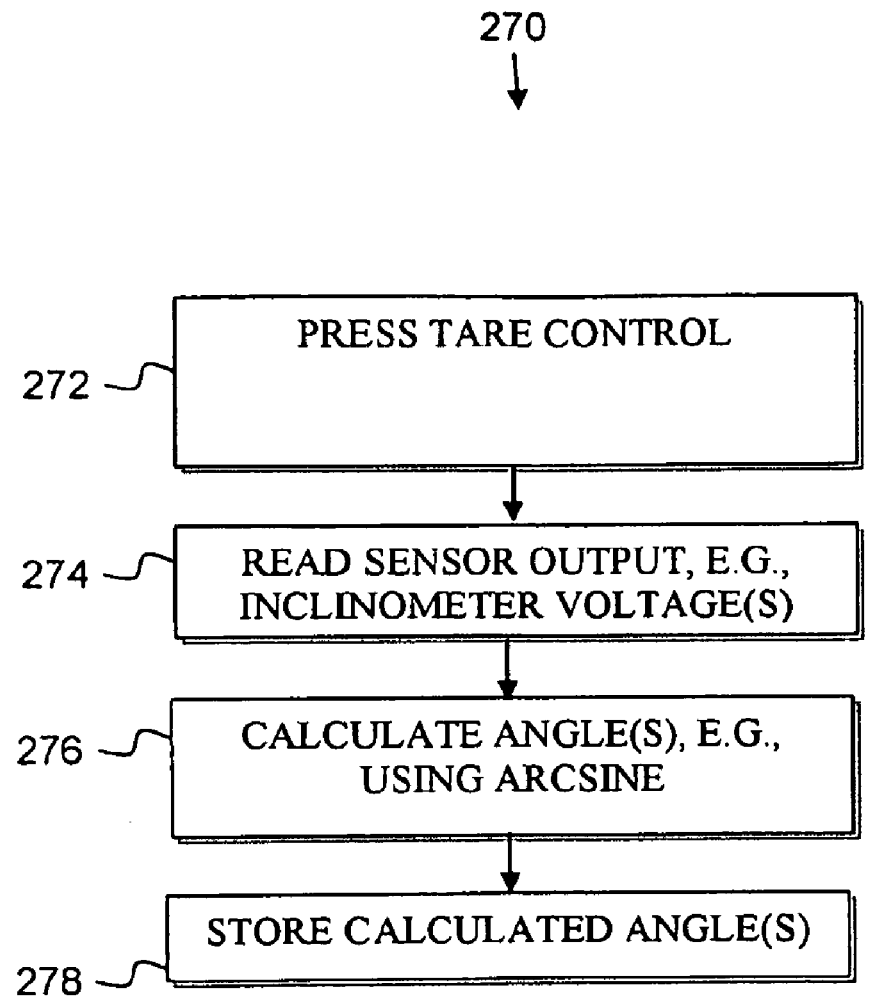
FIG. 17 is a flow chart illustrating a method of implementing an electronic tare to calibrate an assessment device according to aspects of the present invention.

Referring to FIG. 17, an exemplary method 270 is illustrated for allowing a user to set the TARE according to various aspects of the present invention. The user presses the TARE control at 272. The microcontroller or other control electronics reads the voltage from the inclinometer(s) at 274. Angles for each axis are computed at 276, for example, using an arcsine function. The calculated results are then stored at 278.

Figure 18:
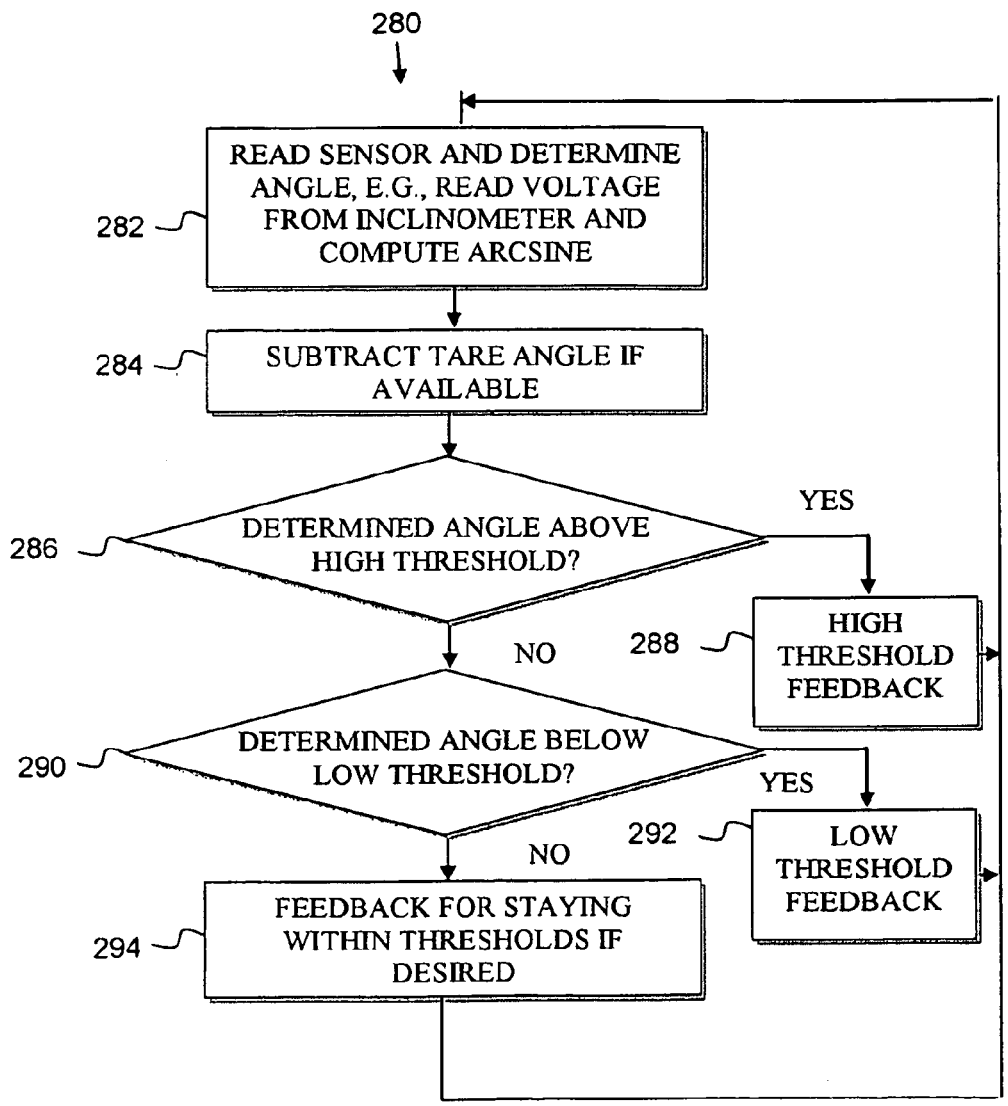
FIG. 18 is a flow chart illustrating a method for using the assessment device according to aspects of the present invention.

Referring to FIG. 18, an exemplary method 280 of providing feedback according to an aspect of the present invention is illustrated. The method 280 is implemented for each axis independently. The sensor is read and a corresponding angle is determined at 282. For example, the voltage of an inclinometer output signal is read and the corresponding angle is calculated, e.g., from the arcsine function. The TARE angle is subtracted from the measured value at 284 if applicable. A decision is made at 286 as to whether the resultant value is above a high threshold. If the resultant value is above the high threshold, high threshold feedback is generated at 288 and the process loops back to read another sensor value at 282. A decision is made at 290 as to whether the resultant value is below a low threshold. If the resultant value is below the low threshold, then low threshold feedback is generated at 292 and the process loops back to read another sensor value at 282. Otherwise, feedback for staying within the threshold range may be provided as desired by the particular application, and the process loops back to read another sensor value at 282.

According to an aspect of the present invention, the output that designates a breach of a threshold does not latch. Transients that trigger the alarm but are quickly corrected are also not latched. Such brief alarms are interpreted as a failure during testing usage, but during training they provide feedback that the user is just on the edge of the threshold. Transients that are too quick to register an alarm are ignored, but human motion is likely too slow to realistically cause such brief transients. However, other arrangements, including latching an alarm or other output indicative of a threshold breach may alternatively be implemented.

The assessment device may be utilized to implement a "pre-training" mode by connecting the assessment device 10 to an object or subject of interest. The assessment device is then utilized for capturing a set of data values that characterize maximum deviations of a desired motion or position with respect to at least one axis without providing feedback. The captured values are saved as a pre-training baseline. The assessment device is then utilized to implement a "training mode" by repeating the position or motion utilizing the assessment device to capture data values that characterize a range of the motion or position. The captured values are compared to predetermined threshold values and feedback is provided to train the movement or position.

The assessment device is then utilized to implement a "post-training" mode by utilizing the assessment device to capture data values that characterize maximum deviations of the desired motion or position with respect to at least one axis as without providing feedback. The data values are saved as a post-training baseline and feedback is provided as to whether the training is becoming more effective towards the desired motion or position based upon a comparison of the post training baseline with the pre-training baseline.

Figure 19:
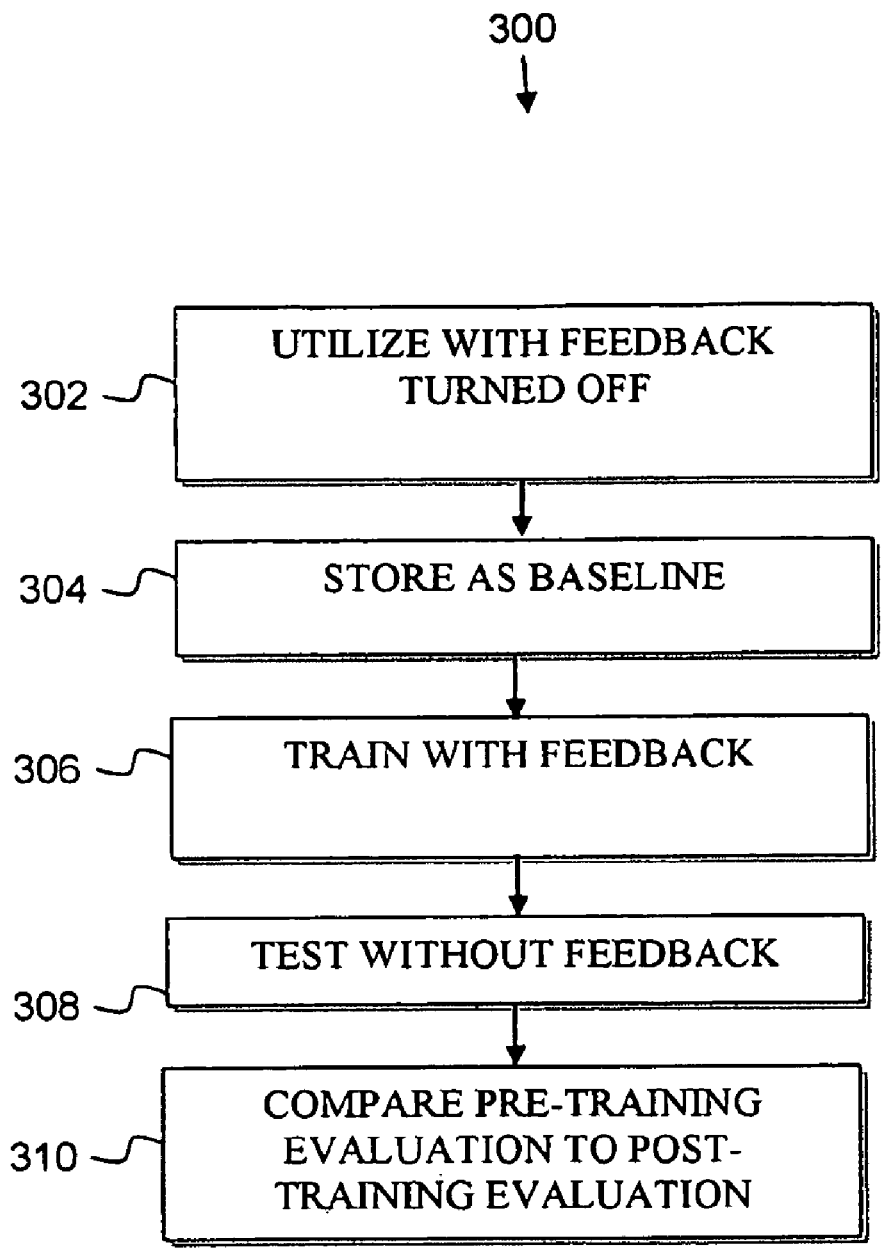
FIG. 19 is a flow chart illustrating a method for using the assessment device for training according to aspects of the present invention.

Referring to FIG. 19, according to various aspects of the present invention, a method 300 of training is provided, which utilizes the assessment device 10.

Thus, the assessment device is utilized to test a position or range of motions while operating in a mode at 302 where no feedback is provided. This "silent" diagnostic mode records peaks in multiple simultaneous directions. For example, using a two-axis inclinometer, the silent diagnostic mode may capture peaks in all four directions simultaneously. However, the outputs are disabled. The sample values, e.g., at least the captured peak values, are stored as a baseline at 304. These pre-training test results identify the range/tolerance of the position/movement.

After establishing a pre-training baseline, a training mode is entered wherein the assessment device is operated in a manner that provides feedback at 306. For example, the baseline may serve as a set of default starting conditions. Thus, in an illustrative example of evaluating a subject standing on one leg, the baseline may suggest that the starting thresholds comprise +/−20 or +20/−10 along one axis but +3/−5 along another axis. Thus, training can be precisely tailored to each direction along each axis from the start of training. As another illustrative example, a subject that suffered a stroke may exhibit one side better than other. As such, different ranges can be identified for the different evaluations.

Regardless of how the process is initiated, feedback is provided to the user, e.g., for breaching an associated threshold. After suitable training, a post-training evaluation is conducted where the test is once again performed without feedback at 308. The results of pre-training evaluations and post-training evaluations are compared at 310. If desired results are not achieved, the process can loop back to 306 and repeat as required to achieve the desired result.

Thus, the method may further comprise repeating the training mode and post training mode to update the post-training baseline. The most recent post-training baseline may then be compared against previously saved post-training baselines and feedback may be provided as to whether the subject is improving over time.

Still further, at least one of the pre-training baseline or the post-training baseline may be stored for a plurality of subjects. The baselines stored for each of a plurality of subjects may be compared and a classification may be implemented to classify the subjects based upon an evaluation of their associated baseline. Still further, during testing or training, inputs may be recorded from at least one other input device. The recorded inputs may be correlated with the data captured from the assessment device and feedback may be provided as to whether there is a detectable correlation between the captured data from the assessment device and the recorded data from the other input device.

In this regard, a diagnostic mode is provided distinct from a training mode. This approach provides an unbiased approach to evaluation and may accelerate training as the subject can start the training process with threshold values at or around the initial conditions instead of guessing at starting thresholds. Moreover, the status of training can be effectively monitored. This baseline may further serve to illustrate the range of motion that is currently being exhibited and provides information to a skilled trainer to show a subject what to try to control so that training is more directed.

For example, using a two-axis inclinometer, during the pre-training diagnostic, two axes are simultaneously measured. This results in recording at least four points including the minimum and maximum values along each axis. These four points (in the present example) can be conceptualized as the corners of a polygon that defines a range that defines the deviations from the position, e.g., posture, motion, etc. During post-training evaluation, the polygons can be compared to ensure that proper improvement is occurring in all directions of interest, e.g., by virtue of a smaller polygon in one or more directions.

According to still further aspects of the present invention, a performance mode of operation may be implemented. In the performance mode, the assessment device automatically progresses its threshold values, e.g., by either tightening or loosening the threshold in one or more directions.

When monitoring the captured values during training, the assessment device may compare the captured values to corresponding threshold values and dynamically update the threshold values based upon the comparison.

Figure 20:
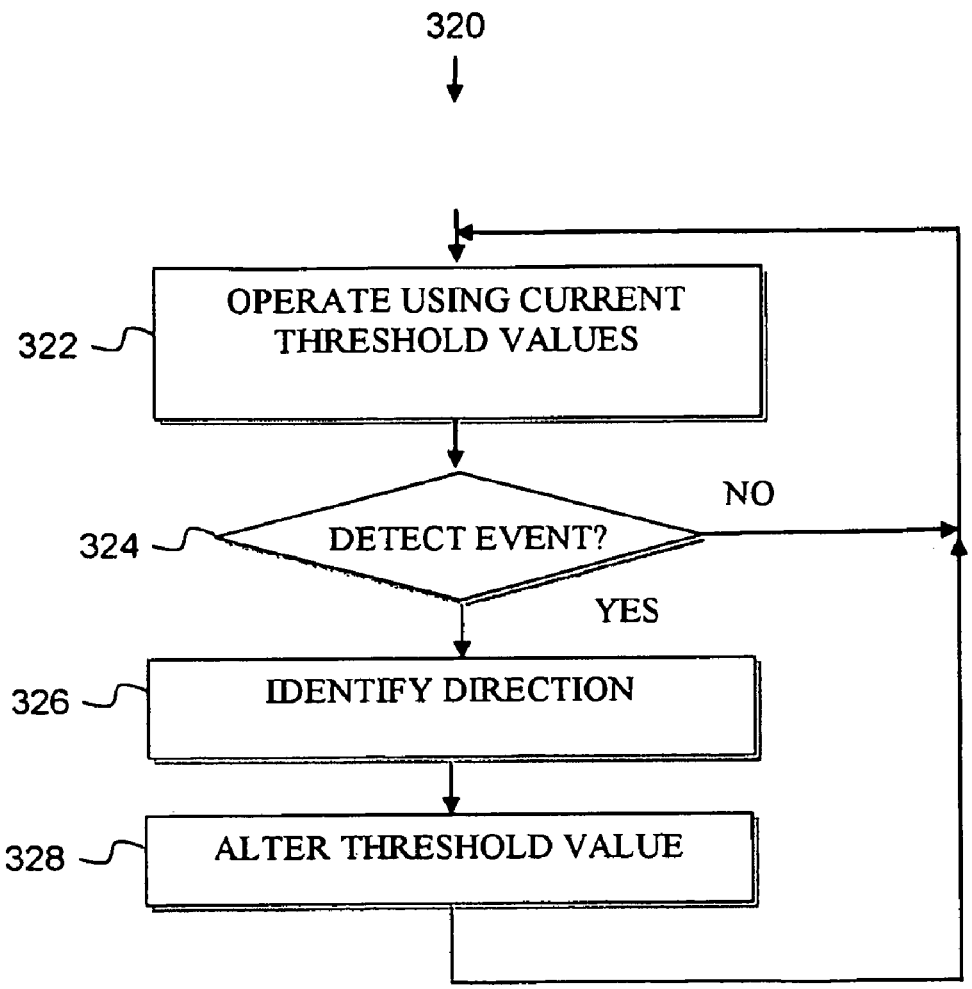
FIG. 20 is a flow chart illustrating a method for performance training according to aspects of the present invention.

Referring to FIG. 20, a method 320 for performance training according to various aspects of the present invention is illustrated. The assessment device is utilized in its normal manner to determine whether its sensor has breached predetermined threshold values at 322. If a predetermined event is detected at 324, then a direction associated with the event is determined at 326 and the threshold value for that direction is changed at 328, e.g., either loosened or tightened from the reference zero orientation. During this process, the actual compared measurements may be further compared to the threshold values. Depending upon how close the measured values get to or exceed the various thresholds, a determination is made as to whether the threshold value is appropriate. The particular determination is likely to be situation specific. For example, under certain circumstances, some breaches may be tolerated while in other situations, fewer or no breaches may be tolerated. Moreover, the extent to which the threshold is breached, the number of breaches, time between breaches and other relevant factors may be considered in automatically, dynamically adjusting the threshold parameter(s).

Still further, the logging capability of the digital implementations of the assessment device may allow for the preservation of number of times that the evaluation is performed. This allows subjects to track improvement over time, and allows trainers to monitor the use of the device, e.g., by subjects performing user training. Still further, the assessment device can log the time, number of breaches and amount of breach. Thus, for example, a trainer can monitor and record how many times a subject gets into bad posture in an 8 hour day or other period, the highest breaches in each direction, how much time was spent beyond each breached threshold, how much time was spent within or between breaches, the number of repetitions of the desired position or movement, etc.

Still further, the logs can serve as a telltale enabling trainers to evaluate whether or not the assessment device is being used properly or not. Moreover, by storing the tare values, the trainer can get a sense of how repeatable the subject is at setting up the assessment device for self training.

According to various aspects of the present invention, comparative data may also be collected and analyzed. Such comparative data may track not only a particular subject or object, but also groups. This allows classification based upon evaluation of breaches. Thus, a trainer may be able to classify a subject based upon their functional evaluation using the assessment device. Thus for example, a subject can be characterized against other individuals or groups of individuals.

While described in general with reference to the use of an inclinometer, other sensing devices may alternatively be used. For example, mercury switches, such as with a curved glass case can be used to trigger an alarm when a threshold is reached. Mercury switches close a circuit when a small quantity of liquid mercury rolls onto two metal posts and fills the space between them. The curvature of the glass and placement of the metal posts determine the thresholds. This design could be used in conjunction with a mechanical taring method.

Further, gyroscopes can be used to determine orientation of the device. A gyroscope creates a torque proportional to the angular velocity it experiences. The angular velocity can then be integrated to estimate angular position. A microcontroller or other suitable control electronics may be used to perform the integrations for 3 orthogonally-mounted gyroscopes.

As yet a further example, the inclinometer may be replaced by an "Upside-down marionette". The user is placed on a platform with 4 cables. The 4 cables attach to a cuff placed on the body part of interest. The cables are wound around tensioning pulleys under the platform. When the user moves the body part, the cables extend or retract. Rotary encoders on the tensioning pulleys record the excursion of the individual cables. A microcontroller or other processing device then converts the excursions of the individual cables to the tilt of the body part and creates feedback for assessment or training.

Other features such as a low battery indicator may be provided on the assessment device to let the user know that the battery must be changed to maintain accurate readings.

Various aspects of the present invention provide an assessment device 10 that is adjustable to accommodate its operating environment. For example, every individual's sacrum is a different shape and is pitched at a different angle. Thus, to achieve a correct/desired position when attached to the sacrum of a subject, the user (with an observer or on their own) may be able to position the device, then configure the device to allow individualization to the unique user. The configuration may be performed using the tare capabilities and/or the programmable features of setting the threshold sets as described more fully herein.

According to various aspects of the present invention, methods are provided for training with an affixable assessment device. An aspect that is relevant to training is repetition. In many instances, proper repetition assures proper training. Providing feedback for approving or disproving a movement pattern or position assures practice that strives for the performance of activities within prescribed tolerances. As noted in greater detail herein, feedback can come in the form of visual, audible, tactile and smell.

Real time feedback provided to the trainee can support or discourage their present movement pattern or position. This feedback may also allow the trainee to learn or retrain their bodies neuromuscular control and positional awareness (proprioception) promoting the desired movement pattern or position. Repetitive training with real-time feedback enhances muscle memory and proper muscular recruitment thereby, training a desired movement pattern as the bodies chosen way of performing an activity or positioning itself. The use of an affixable assessment device to alert the user of incorrect motion assists in the assurance that proper training is being conducted by the device user.

The assessment device may also be coupled to subdevices. For example, a headgear device may allow multi-dimensional cuing. A subdevice may for example, consist of means of providing audible and/or visual feedback to the user. It is connected to the sensing device either with a tethered connection or a wireless connection. For example, headgear may use four or more speakers to create audible sounds. Electrical signals are sent to the speakers to create the perception by the user of the sounds coming from a direction (front, back, left, right, up, or down), similar to surround sound systems used in home and movie theater sound systems. The headgear may also include a component that lies within the field of view of the user. This component contains several lights placed in different parts of the field of view, capable of sending visual cues with directionality (up, down, left, right).

A vibration cuff may also be utilized to allow multi-dimensional cuing. This subdevice consists of means of providing tactile feedback to the user. It is connected to the sensing device either with a tethered connection or a wireless connection. The vibration cuff is affixed to the user either through the same means as the sensing device, or can be affixed using its own means. The vibration cuff contains several embedded vibrators, each similar to those inside mobile phone and pagers, which give tactile feedback to the user with directionality. The locations of the individual vibrators add the directionality of feedback to the user. The cuff may be placed on the same body part of interest, or it may be placed on a different body part of the user that is more sensitive to tactile feedback.

Accordingly, assessment devices are provided, which may be useful in a number of varied applications, such as sports training (professional and amateur). Assessment devices according to various aspects of the present invention also find use for positional awareness during use with other strengthening equipment including but not limited to weight training, medicine ball toss, etc. Assessment devices according to various aspects of the present invention also find use in gait training, theraband, Swiss ball, body blade and pike exercises. Assessment devices according to various aspects of the present invention also find use with technique training including but not limited to swinging club or bat. For example, by affixing the assessment device to arm when throwing, a subject can be trained to keep the throwing elbow elevated, keep shoulders from dropping when hitting, etc.

The assessment device may be used for static monitoring. For example, in the case of a golfer training application, the assessment device may be used to assess/train the golfer in the correct postures at various instants during the swing (e.g. addressing the ball, ¼ backswing position, full backswing position, follow-through position).

Assessment devices according to various aspects of the present invention also find use in dance, music and other artistic and performing arts training for providing postural training and positioning awareness. Still further uses may comprise posture training, which may include, for example, sitting, standing, gaming, etc. Students/academic Institutions may also utilize the assessment devices according to various aspects of the present invention in computer labs and lecture halls, etc The assessment devices according to various aspects of the present invention may also be utilized for all types of rehabilitation applications that protect and promote good functional positioning of the body part of interest. The assessment devices according to various aspects of the present invention may also be utilized for occupational safety training, such as for including but not limited to seated posture during sitting, shoulder position while using a mouse, head tilt while making phone calls, driving, overhead work, lifting activities, assembly line work, awareness needs for body part of interest, e.g., for postural retraining, etc. Still further, assessment devices according to various aspects of the present invention may be used in nursing homes and other care facilities where a patient may find themselves in a precarious position. The alarm that detects a breach of threshold may thus be used to designate an alarm to a staff that the patient is in need of assistance.

In the training of amputees to use new limbs, especially lower extremities, the assessment device 10 can be affixed to a variety of anatomical locations to provide feedback on alignment and stability during training and acclimation to the new extremities. With the tare functionality, the assessment device 10 can be used to cue the wearer to horizontal position for the limbs or body regardless of the orientation of the component housing because the sensor device can be electrically and/or mechanically calibrated relative to the sensor/assessment device housing. It can also be used in the core training position to show if core muscles are properly engaged. The tare functionality can allow a more coarse setting during early training and acclimation sessions and progression to more sensitive settings as the client progresses through acclimation. This device and method has the potential to reduce physical therapy sessions and allows home therapy to progress with user feedback.

The assessment device 10 according to various aspects of the present invention may also be utilized in military training and evaluation. Still further, the assessment device 10 according to various aspects of the present invention may be utilized for Veterinarian medicine, Equine/Horse racing applications and other animal training practices:

Still further, the assessment device 10 may be utilized in nursing homes, assisted living centers, hospitals and other health care facilities as movement monitors, alarms etc.

As further illustrative examples, the assessment device may be placed on an object instead of a person for evaluation or alarm purposes. For example, the assessment device may be utilized for awareness of position of the object. For example, the assessment device may be utilized to detect the tipping of walker, wheelchair or other assistive device. The assessment device may be used to detect a basketball rim bent after dunk, whether gymnastics equipment is out of alignment, whether an archery target not in right position, etc. As further examples, the assessment device may be utilized to monitor whether a boat, plane, truck etc. is tipping as it is being loaded or unloaded.

The logic and functions described herein may be implemented in software, e.g., as executed on a suitable microcontroller. Alternatively, the logic and functions described herein may be implemented in hardware, e.g., using comparators, etc. Further, the logic and functions herein may be implemented by a combination of hardware and software.

The flowchart and block diagrams in the Figures illustrate the architecture, functionality, and operation of possible implementations of systems, methods and computer program products according to various embodiments of the present invention. In this regard, one or more blocks in the flowchart or block diagrams may represent a component, segment, or portion of code, which comprises one or more executable instructions for implementing the specified logical function(s). In some alternative implementations, the functions noted in the blocks may occur out of the order noted in the figures. For example, two blocks shown in succession may, in fact, be executed substantially concurrently or in the reverse order.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The description of the present invention has been presented for purposes of illustration and description, but is not intended to be exhaustive or limited to the invention in the form disclosed. Many modifications and variations will be apparent to those of ordinary skill in the art without departing from the scope and spirit of the invention.

Having thus described the invention of the present application in detail and by reference to embodiments thereof, it will be apparent that modifications and variations are possible without departing from the scope of the invention defined in the appended claims.

What is claimed is:

1. An assessment device for evaluating positions of interest comprising:
    a sensing device configured to measure angles relative to at least one axis of a predefined sensor orientation and to output information indicative of detected angles with respect to each measured axis;
    a sensor component having:
        a first member that is mountable to an object or subject of interest; and
        a second member configured such that the sensing device secures thereto, wherein the second member is repositionable in at least one dimension with respect to the first member so as to reorient the sensing device, and hence the predefined sensor orientation, with respect to the first member;
    a controller for processing the information output by the sensing device;
    a threshold setting control coupled to the controller for setting at least one user-selectable threshold parameter, each user-selectable threshold parameter associated with a corresponding axis of interest;
    a calibration setting control coupled to the controller for instigating an electronic calibration process; and
    an output device coupled to the controller;
    wherein:
        the first member of the sensor component is mountable to the object or subject of interest at a user-defined orientation with respect to a principle axis of a desired evaluation environment;
        the second member of the sensor component is correspondingly positioned and secured with respect to the first member of the sensor component so that the sensing device is aligned to a second orientation different from the user-defined orientation of the first member, providing at least a coarse mechanical tare calibration;
        the controller is configured to determine a range of angles based upon at least one user-selected threshold parameter entered via the threshold setting control and the user-defined orientation; and
        the controller is configured to implement an operational mode that monitors the output information of the sensing device, determines angle measurements from the monitored output information of the sensing device, compares the determined angle measurements to the determined range of angles and initiates the output device to convey information based upon the comparison of the determined angle measurements and the determined range of angles.

2. The assessment device according to claim 1, wherein:
the controller is further configured to perform at least a fine tuning electrical tare calibration upon actuation of the calibration setting control by:
reading the output information of the sensing device while the first member of the sensor component is held at the user-defined orientation;
comparing the output information read out by the controller with an ideal position derived from the pre-defined orientation of the sensing device to derive a calibration offset; and
storing the calibration offset; and
the controller is further configured to initiate the output device to convey information based upon the comparison of the determined angle measurements, the determined range of angles and the derived calibration offset.

3. The assessment device according to claim 1, wherein:
the first member of the sensor component comprises a plate that is mountable at a user-defined orientation;
the second member of the sensor component comprises a gimbal configured such that the sensing device is movable with respect to at least one axis of the gimbal so that the sensing device may be reoriented relative to the plate.

4. The assessment device according to claim 1, wherein the output device outputs at least one of a visual, audible, tactile or olfactory cue that is triggered by the controller, wherein the output comprises a pattern that varies depending upon the axis and direction of a breach of a corresponding threshold.

5. The assessment device according to claim 1, wherein the controller comprises a portable computing device and the sensing device comprises a multi-axis inclinometer that is coupled to the portable computing device.

6. The assessment device according to claim 1, wherein the controller is configured to:
program a high threshold value that determines an upper range of measured angle values relative to a corresponding axis of the user-defined orientation;
program a low threshold value that determines a lower range of measured angle values relative to the corresponding axis of the user-defined orientation; and
control the output device such that a high threshold breach is indicated differently from a low threshold breach.

7. The assessment device according to claim 1, further comprising coupling a global positioning system device to the controller for correlation of angle measurement values to information read from the global positioning system device.

8. The assessment device according to claim 1, further comprising storage that is coupled to the controller, wherein the controller logs measured data values for analysis of breach of thresholds as a function of time or endurance.

9. The assessment device according to claim 1, wherein the controller is configured to operate in a first mode where the output device is selectively activated depending upon a detected breach of a threshold, and a second mode where the output is disabled so that the subject receives no feedback as to their position relative to the programmed thresholds.

10. An assessment device for evaluating positions of interest comprising:
a sensing device configured to measure angles relative to at least three orthogonal axes of a reference orientation and to output information indicative of detected angles with respect to each measured axis;
a controller for processing the information output by the sensing device;
a threshold setting control coupled to the controller for setting at least one user-selectable threshold parameter, each user-selectable threshold parameter associated with a corresponding axis of interest;
a calibration setting control coupled to the controller for instigating an electronic calibration process; and
an output device coupled to the controller;
wherein:
the controller is configured to perform an electronic calibration upon actuation of the calibration setting control by:
moving the sensing device to a first known position;
reading the output information of the sensing device while the sensing device is in the first known position;
determining the orientation of the sensing device relative to its reference orientation;
defining a first vector relative to the first known position and reference orientation;
moving the sensing device to a second known position;
reading the output information of the sensing device while the sensing device is in the second known position;
determining the orientation of the sensing device relative to its reference orientation;
defining a second vector relative to the second known position and reference orientation;
computing an orientation of the sensing device based upon the first and second vectors; and
determining a calibration offset based upon the determined orientation and the reference orientation;
the controller is configured to determine a range of angles based upon at least one user-selected threshold parameter entered via the threshold setting control and the user-defined orientation; and
the controller is configured to implement an operational mode that monitors the output information of the sensing device, determines angle measurements from the monitored output information of the sensing device, compares the determined angle measurements to the determined range of angles and initiates the output device to convey information based upon the comparison of the determined angle measurements, the determined range of angles and the derived calibration offset.

11. The device according to claim 10, wherein the output device comprises at least one of a visual, audible, tactile or olfactory cue that is triggered by the controller in response to detecting a breach of at least one threshold.

12. The assessment device according to claim 10, wherein the output device outputs at least one of a visual, audible, tactile or olfactory cue that is triggered by the controller, wherein the output comprises a pattern that varies depending upon the axis and direction of a breach of a corresponding threshold.

13. The assessment device according to claim 10, wherein the controller comprises a portable computing device and the sensing device comprises a multi-axis inclinometer that is coupled to the portable computing device.

14. The assessment device according to claim 10, wherein the controller is configured to:
program a high threshold value that determines an upper range of measured angle values relative to a corresponding axis of the user-defined orientation;

program a low threshold value that determines a lower range of measured angle values relative to the corresponding axis of the user-defined orientation; and
control the output device such that a high threshold breach is indicated differently from a low threshold breach.

15. The assessment device according to claim 10, further comprising coupling a global positioning system device to the controller for correlation of angle measurement values to information read from the global positioning system device.

16. The assessment device according to claim 10, further comprising storage that is coupled to the controller, wherein the controller logs measured data values for analysis of breach of thresholds as a function of time or endurance.

17. The assessment device according to claim 10, wherein the controller is configured to operate in a first mode where the output device is selectively activated depending upon a detected breach of a threshold, and a second mode where the output is disabled so that the subject receives no feedback as to their position relative to the programmed thresholds.

18. A method of training using an assessment device for evaluating positions of interest comprising:
providing an assessment device comprising:
a sensing device configured to measure angles relative to at least one axis of a predefined sensor orientation and to output information indicative of detected angles with respect to each measured axis; and
a sensor component having:
a first member; and
a second member configured such that the sensing device secures thereto, wherein the second member is repositionable in at least one dimension with respect to the first member so as to reorient the sensing device, and hence a predefined sensor orientation, with respect to the first member;
connecting the assessment device to an object or subject of interest, by:
mounting the first member of the sensor component to the object or subject of interest at a user-defined orientation with respect to a principle axis of a desired evaluation environment; and performing a calibration by:
positioning the second member of the sensor component with respect to the first member of the sensor component so that the sensing device is aligned to a second orientation different from the user-defined orientation providing at least a coarse mechanical tare calibration;
implementing a pre-training mode by:
capturing a set of data values that characterize maximum deviations of a desired motion or position with respect to at least one axis without providing feedback; and
saving the captured values as a baseline;
implementing a training mode by:
repeating the position or motion;
utilizing the assessment device to capture data values that characterize a range of the motion or position;
comparing the captured values to predetermined threshold values; and
providing a feedback to train the movement or position; and
implementing a post-training mode by:
utilizing the assessment device to capture data values that characterize maximum deviations of the desired motion or position with respect to at least one axis as without providing feedback;
saving the data values as a post-training baseline; and
providing feedback as to whether the training is becoming more effective towards the desired motion or position based upon a comparison of the post training baseline with the pre-training baseline.

19. The method according to claim 18, wherein the values of the pre-training baseline are utilized to establish reference thresholds for training.

20. The method according to claim 18, further comprising:
monitoring the captured values during training;
comparing the captured values to corresponding threshold values; and
dynamically updating the threshold values based upon the comparison.

21. The method according to claim 18, further comprising:
repeating the training mode and post training mode to update the post-training baseline;
comparing the most recent post-training baseline against previously saved post-training baselines; and
providing feedback as to whether the subject is improving over time.

22. The method according to claim 18, further comprising:
storing at least one of the pre-training baseline or the post-training baseline for a plurality of subjects;
comparing the baselines stored for each of a plurality of subjects; and
classifying the subjects based upon an evaluation of their associated baseline.

23. The method according to claim 18, wherein implementing a training mode further comprises:
recording inputs from at least one other input device;
correlating the inputs form the at least one other device with the data captured from the assessment device; and
providing feedback as to whether there is a detectable correlation between the captured data from the assessment device and the recorded data from the other input device.

24. A method of training using an assessment device for evaluating positions of interest comprising:
performing an electronic calibration of a sensing device of an assessment device, wherein the sensing device comprises a sensor for measuring at least one angle and the electronic calibration is performed by:
moving the sensing device to a first known position;
reading output information of the sensing device while the sensing device is in the first known position;
determining the orientation of the sensing device relative to its reference orientation;
defining a first vector relative to the first known position and reference orientation;
moving the sensing device to a second known position;
reading the output information of the sensing device while the sensing device is in the second known position;
determining the orientation of the sensing device relative to its reference orientation;
defining a second vector relative to the second known position and reference orientation;
computing an orientation of the sensing device based upon the first and second vectors; and
determining a calibration offset based upon the determined orientation and the reference orientation;
implementing a pre-training mode by:
connecting the assessment device to an object or subject of interest;

capturing a set of data values that characterize maximum deviations of a desired motion or position with respect to at least one axis without providing feedback; and saving the captured values as a baseline;

implementing a training mode by:

repeating the position or motion;

utilizing the assessment device to capture data values that characterize a range of the motion or position;

comparing the captured values to predetermined threshold values; and providing a feedback to train the movement or position; and implementing a post-training mode by:

utilizing the assessment device to capture data values that characterize maximum deviations of the desired motion or position with respect to at least one axis as without providing feedback;

saving the data values as a post-training baseline; and providing feedback as to whether the training is becoming more effective towards the desired motion or position based upon a comparison of the post training baseline with the pre-training baseline.

25. The method according to claim 24, wherein the values of the pre-training baseline are utilized to establish reference thresholds for training.

26. The method according to claim 24, further comprising:
monitoring the captured values during training;
comparing the captured values to corresponding threshold values; and
dynamically updating the threshold values based upon the comparison.

27. The method according to claim 24, further comprising:
repeating the training mode and post training mode to update the post-training baseline;
comparing the most recent post-training baseline against previously saved post-training baselines; and
providing feedback as to whether the subject is improving over time.

28. The method according to claim 24, further comprising:
storing at least one of the pre-training baseline or the post-training baseline for a plurality of subjects;
comparing the baselines stored for each of the plurality of subjects; and
classifying the subjects based upon an evaluation of their associated baseline.

29. The method according to claim 24, wherein implementing a training mode further comprises:
recording inputs from at least one other input device;
correlating the inputs form the at least one other device with the data captured from the assessment device; and
providing feedback as to whether there is a detectable correlation between the captured data from the assessment device and the recorded data from the other input device.

* * * * *